(12) United States Patent
Zakai et al.

(10) Patent No.: US 10,786,355 B2
(45) Date of Patent: Sep. 29, 2020

(54) MITRAL VALUE PROSTHESIS WITH ATRIAL ANCHORING

(71) Applicant: Edwards Lifesciences AG, Nyon (CH)

(72) Inventors: Avraham Zakai, Tel Aviv-Jaffa (IL); David Mishaly, Shoham (IL); Dan Rottenberg, Haifa (IL); David Alon, Zichron Yaacov (IL)

(73) Assignee: Edwards Lifesciences AG, Nyon (CH)

( * ) Notice: Subject to any disclaimer, the term of this patent is extended or adjusted under 35 U.S.C. 154(b) by 125 days.

(21) Appl. No.: 15/866,338

(22) Filed: Jan. 9, 2018

(65) Prior Publication Data
US 2018/0125645 A1    May 10, 2018

Related U.S. Application Data

(63) Continuation of application No. 14/673,612, filed on Mar. 30, 2015, now Pat. No. 9,861,480, which is a continuation of application No. 13/910,886, filed on Jun. 5, 2013, now Pat. No. 8,992,605, which is a continuation of application No. 12/761,225, filed on Apr. 15, 2010, now Pat. No. 8,460,370, which is a continuation of application No. 11/227,642, filed on Sep. 14, 2005, now Pat. No. 7,704,277.

(60) Provisional application No. 60/657,919, filed on Mar. 3, 2005, provisional application No. 60/609,345, filed on Sep. 14, 2004.

(51) Int. Cl.
*A61F 2/24*     (2006.01)
*A61B 17/00*    (2006.01)
*A61B 17/12*    (2006.01)

(52) U.S. Cl.
CPC ........ *A61F 2/246* (2013.01); *A61B 17/00234* (2013.01); *A61F 2/2466* (2013.01); *A61B 17/12013* (2013.01); *A61B 2017/00783* (2013.01); *A61B 2017/00867* (2013.01); *A61F 2/2412* (2013.01); *A61F 2210/0014* (2013.01); *A61F 2210/0061* (2013.01); *A61F 2210/0066* (2013.01)

(58) Field of Classification Search
USPC ... 623/1.24, 2.1, 2.11, 2.12, 2.14, 2.36, 2.37
See application file for complete search history.

(56) References Cited

U.S. PATENT DOCUMENTS

| | | | |
|---|---|---|---|
| 5,312,341 | A | 5/1994 | Turi |
| 5,332,402 | A | 7/1994 | Teitelbaum |
| 5,738,649 | A | 4/1998 | Macoviak |
| 6,165,183 | A | 12/2000 | Kuehn et al. |
| 6,182,664 | B1 | 2/2001 | Cosgrove |
| 6,241,728 | B1 | 6/2001 | Gaiser et al. |
| 6,269,819 | B1 | 8/2001 | Oz et al. |
| 6,482,224 | B1 | 11/2002 | Michler et al. |

(Continued)

*Primary Examiner* — Yashita Sharma

(57) ABSTRACT

A method of treating a mitral valve without open-heart surgery is disclosed. An expandable prosthesis comprises an anchoring portion and an occluding member coupled to the anchoring portion. The prosthesis is loaded into a distal end of a delivery catheter and advanced through a femoral vein and through a pre-made puncture in an atrial septum. The occluding member is then positioned in the mitral valve and the anchoring portion is positioned in the left atrium for maintaining the occluding member between the leaflets of the mitral valve. After deployment, the occluding member prevents blood from flowing from the left ventricle to the left atrium during systole.

8 Claims, 22 Drawing Sheets

(56) References Cited

U.S. PATENT DOCUMENTS

| | | |
|---|---|---|
| 6,629,534 B1 | 10/2003 | St. Goar et al. |
| 6,730,118 B2 | 5/2004 | Spenser et al. |
| 6,758,830 B1 | 7/2004 | Schaer et al. |
| 2002/0107531 A1 | 8/2002 | Schreck et al. |
| 2003/0120340 A1 | 6/2003 | Liska et al. |
| 2004/0152947 A1 | 8/2004 | Schroeder et al. |
| 2004/0162514 A1 | 8/2004 | Alferness et al. |
| 2004/0260389 A1* | 12/2004 | Case ............. A61F 2/2418 623/1.24 |
| 2008/0243245 A1* | 10/2008 | Thambar ......... A61F 2/2418 623/2.11 |

* cited by examiner

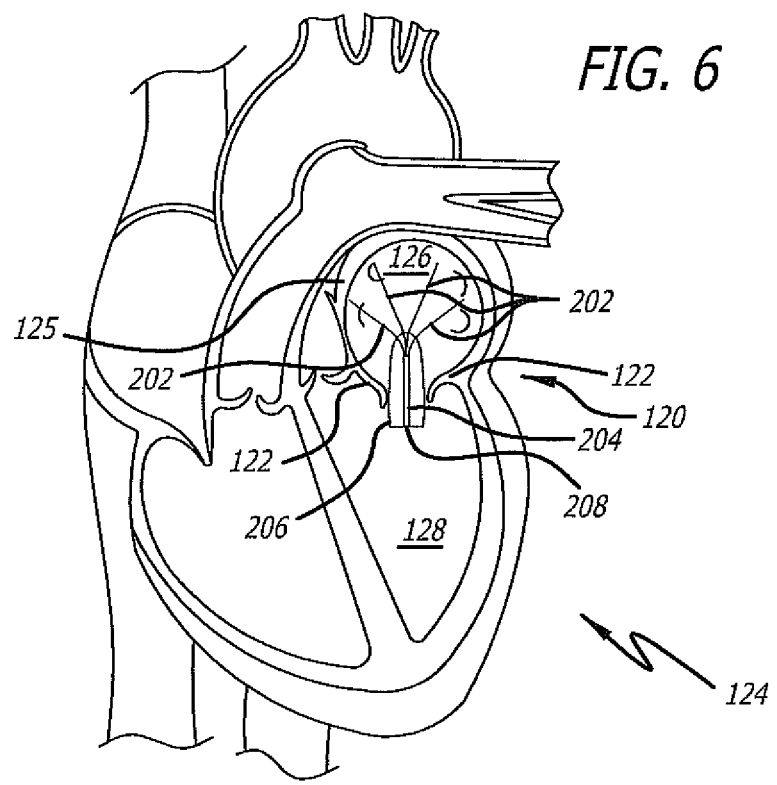
FIG. 6
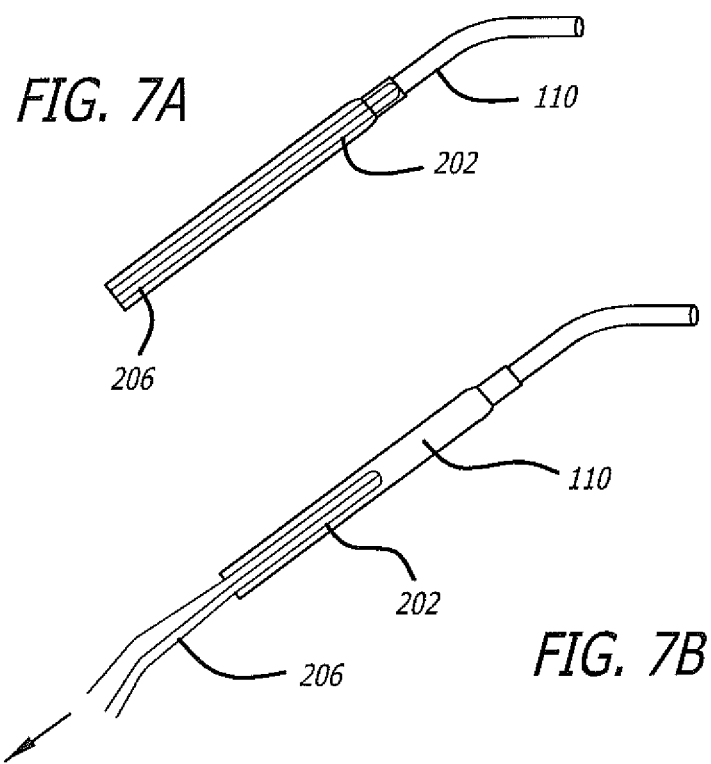
FIG. 7A
FIG. 7B

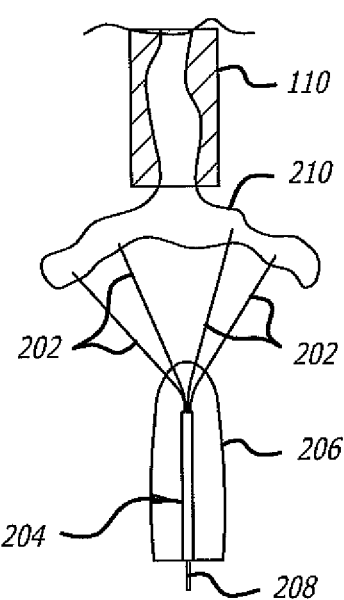 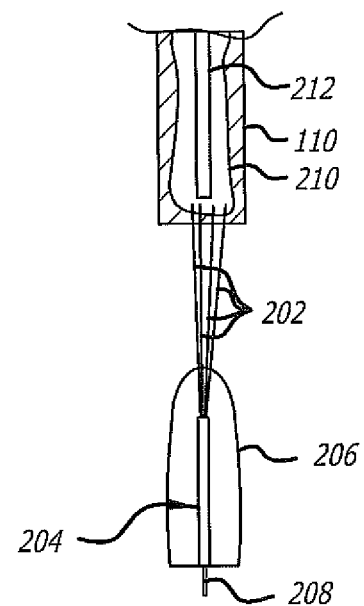
FIG. 8A  FIG. 8B
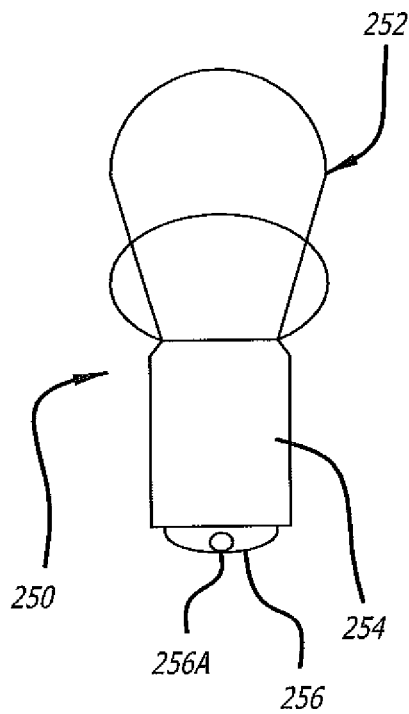 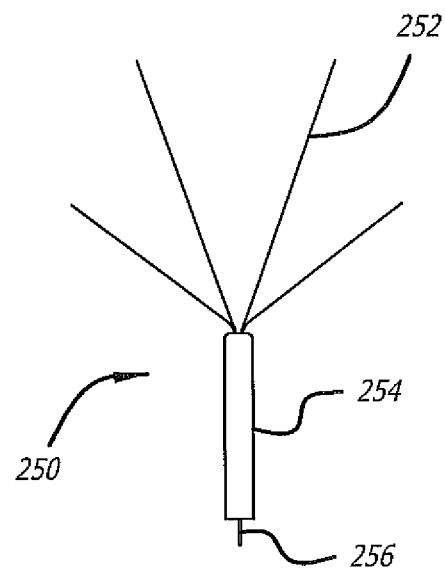
FIG. 9A  FIG. 9B

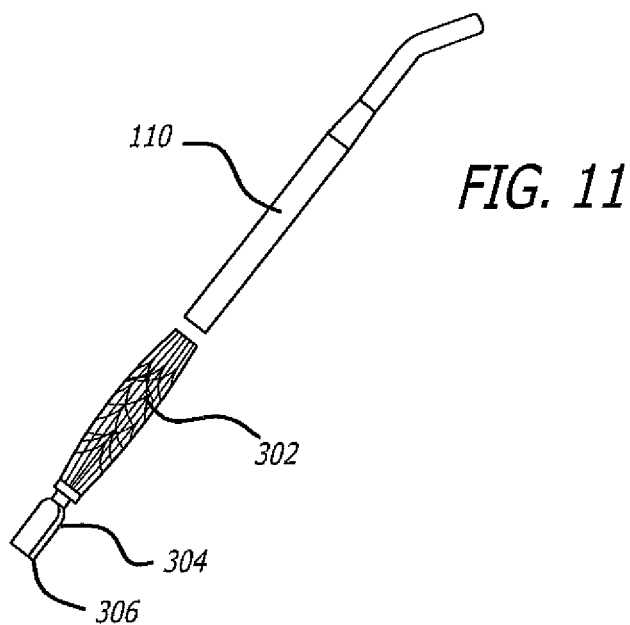
FIG. 11
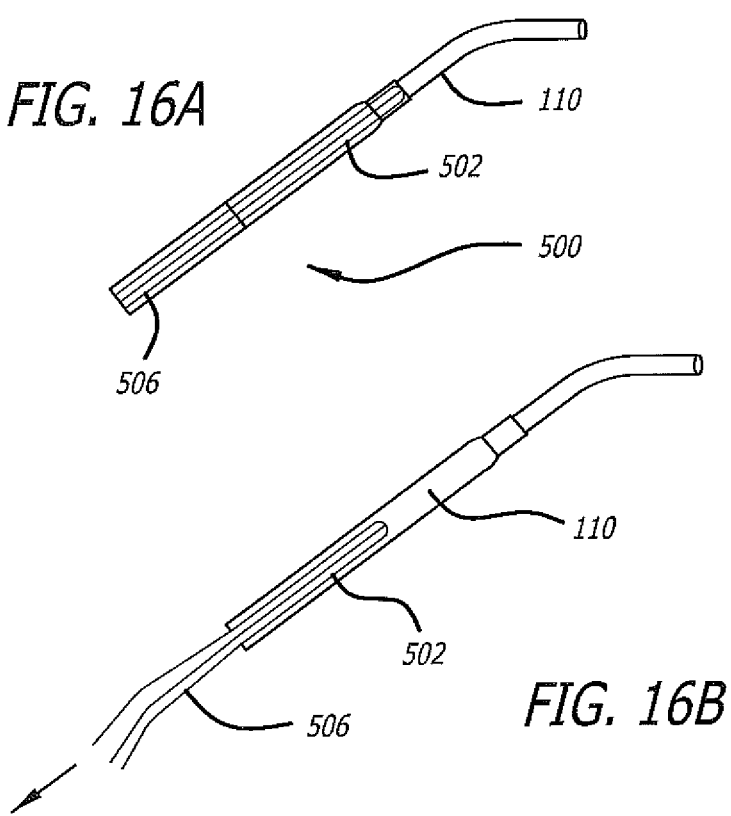
FIG. 16A
FIG. 16B

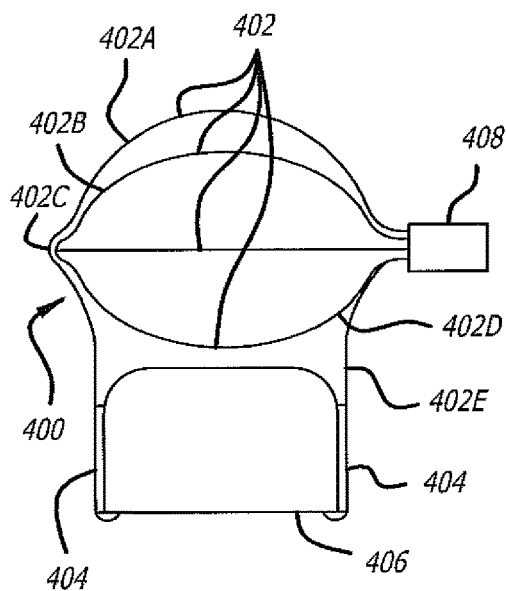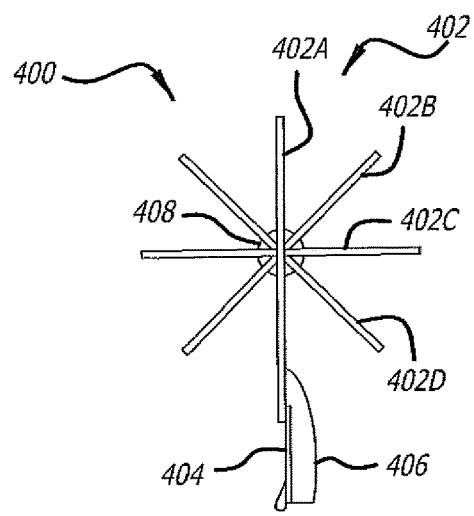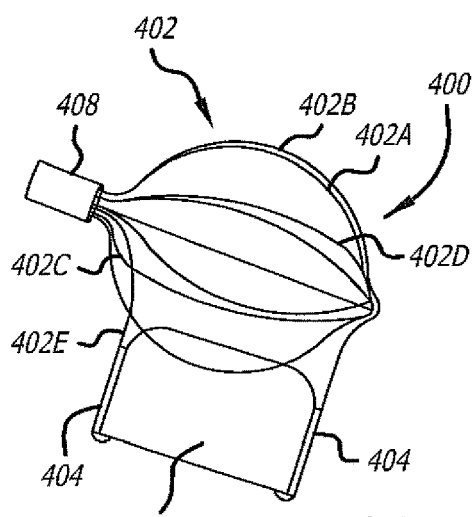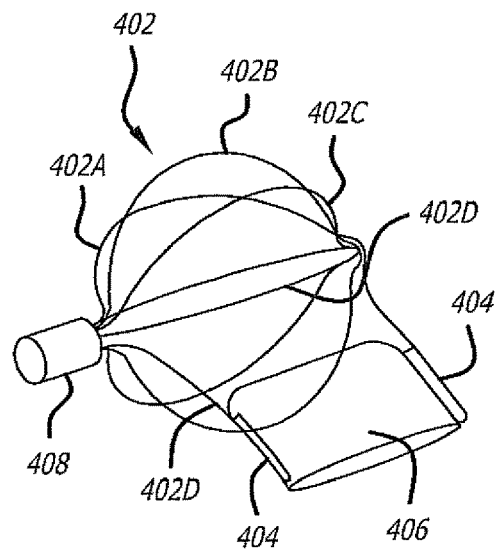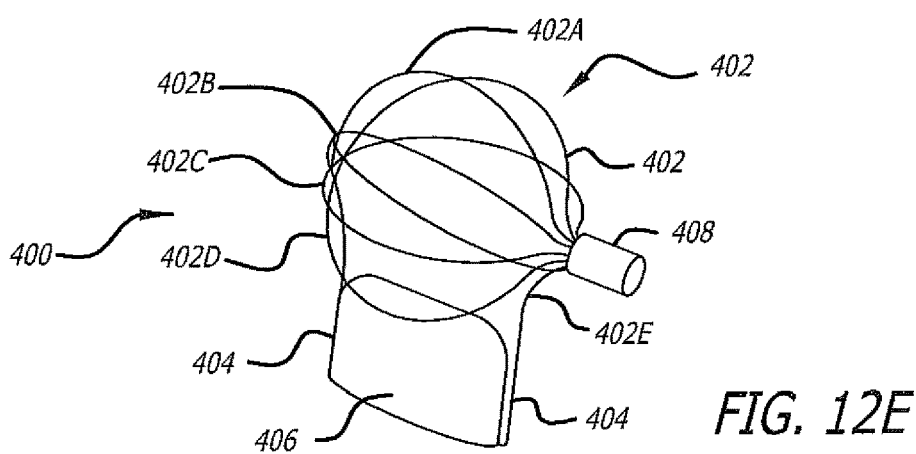

MITRAL VALUE PROSTHESIS WITH ATRIAL ANCHORING

RELATED APPLICATIONS

This application is a continuation of U.S. patent application Ser. No. 14/673,612, filed Mar. 30, 2015, now U.S. Pat. No. 9,861,480, which is a continuation of U.S. patent application Ser. No. 13/910,886, filed Jun. 5, 2013, now U.S. Pat. No. 8,992,605, which is a continuation of U.S. patent application Ser. No. 12/761,225, filed Apr. 15, 2010, now U.S. Pat. No. 8,460,370, which is a continuation of U.S. patent application Ser. No. 11/227,642, filed Sep. 14, 2005, now U.S. Pat. No. 7,704,277, which claims the benefit of U.S. patent application Ser. No. 60/609,345 filed Sep. 14, 2004 and U.S. patent application Ser. No. 60/657,919 filed Mar. 3, 2005; the entire disclosures all of which are incorporated by reference herein.

BACKGROUND OF THE INVENTION

The mitral valve is one of the most crucial of the four valves of the human heart, preventing the regurgitation of blood from the left ventricle into the left atrium during contraction of the heart. Located between the left atrium and the left ventricle, the mitral valve includes two leaflets positioned to block blood flow in a closed state while allowing blood flow in an opened state.

The mitral valve is opened and closed by a pressure differential between the left atrium and left ventricle and by a complex network of collagenous cord-like structures called chordae tendineae that extend from the free edges of the mitral valve leaflets to the papillary muscles on the ventricular wall of the heart. As the papillary muscles contract, they pull on the leaflets and thereby open the mitral valve, allowing blood to flow into the left ventricle. As the papillary muscles relax, the pull on the leaflets is reduced, causing the mitral valve to close and thereby block blood flow into the left ventricle.

Normal operation of the mitral valve can be impaired when the valve leaflets fail to coapt or fully close, allowing regurgitated blood to flow back into the left atrium. This mitral valve regurgitation is often caused by a congenital valve defect or by changes to the heart geometry due to disease. For example, an infection may cause the mitral valve annulus to enlarge and thereby change the position and orientation of the valve leaflets. In another example, a mitral valve defect may cause prolapse or a mismatch of the leaflets, allowing blood flow to regurgitate back into the left atrium.

One early approach to treatment of an insufficient mitral valve involved surgical replacement with an artificial valve. In these procedures, open-heart surgery was typically performed on the patient to replace the faulty valve with either a mechanical or biologically derived valve. While this treatment procedure has been improved with time, significant limitations still exist. For example, the removal and replacement of a mitral valve is highly invasive and therefore greatly increases the risk of serious complications such as infection or rejection.

Other surgical techniques have been developed to reduce the amount of heart remodeling necessary with valve replacement. One such technique is known as bowtie repair, in which a center region of each mitral valve leaflet is sutured together. Another technique involves creating a placation around the valve annulus, thereby reducing the cross-sectional area of the valve annulus. While these techniques require less remodeling than valve replacement, a substantial amount of remodeling is still required. Further, it can be difficult to evaluate the efficacy of the surgical procedure before the conclusion of the surgery.

In yet another technique, an annuloplasty ring is sewn within the annulus of the mitral valve. Since the diameter of the annuloplasty ring is smaller than the diameter of the mitral valve annulus, the leaflets of the valve are moved together, increasing coaptation. In addition to also being highly invasive, annuloplasty rings generally distort the natural curved shape of the mitral valve and can further limit the contractility of the annulus.

While the techniques described above have been used with some success for the treatment of mitral valve deficiencies, additional treatment procedures are needed that require little or no remodeling of the heart. Further, additional treatments are needed that can be performed with minimal invasiveness and yet can more effectively reduce or eliminate mitral valve regurgitation.

OBJECTS AND SUMMARY OF THE INVENTION

It is an object of the present invention to overcome the limitations of the prior art.

It is an object of the present invention to provide an improved method and device for treating mitral valve regurgitation.

It is another object of the present invention to provide a prosthesis device that reduces regurgitation of blood into the left atrium.

It is yet another object of the present invention to provide a prosthesis device that can be delivered and deployed percutaneously within a patient.

It is another object of the present invention to provide a prosthesis device that can dynamically fill gaps between mitral valve leaflets.

It is another object of the present invention to provide a prosthesis device that can reduce most pathologies of mitral valve regurgitation.

The present invention seeks to achieve these objects, as well as others not specifically enumerated here, by providing a prosthesis that can be implanted within a heart to at least partially block gaps that may be present between the two mitral valve leaflets. In one preferred embodiment, the prosthesis includes an anchoring ring that expands within the left atrium to anchor the prosthesis and a pocket member fixed to the anchoring ring. The pocket member is positioned within the mitral valve, between the leaflets so that an open side of the pocket member is positioned within the left ventricle. When the mitral valve is open, blood flows past the pocket member, maintaining the pocket member in a collapsed state. When the mitral valve closes, the backpressure of the blood pushes into the pocket member, expanding the pocket member to an inflated shape. The mitral valve leaflets contact the expanded pocket member, allowing the prosthesis to block at least a portion of the openings between the leaflets, thereby minimizing regurgitated blood flow into the left atrium.

Another preferred embodiment of the present invention provides device for treating valve regurgitation comprising:

a coaptation member sized for placement at least partially between leaflets of a valve, said coaptation member having an expanded state and a deflated state and having a length substantially equal to a commissure of said leaflets; and an anchoring structure connected to said coaptation member, said anchoring structure having a compressed state sized to fit within a delivery catheter and an expanded state sized for fixation on at least a portion of a wall of a chamber adjacent said valve.

Another preferred embodiment of the present invention provides a method of treating valve regurgitation comprising:

loading a prosthesis within a delivery catheter, said prosthesis including an anchoring portion and a coaptation portion;

advancing said delivery catheter to a chamber of a heart;

deploying said coaptation portion within a valve;

expanding said anchoring portion to contact a wall of said chamber; and supporting said coaptation portion within a commissure of said valve.

Another preferred embodiment of the present invention provides a device for substantially blocking blood flow in a valve during systole comprising:

a flexible member having a lateral dimension;

a support member coupled to said flexible member and shaped to position said lateral dimension of said flexible member along a commissural length of a leaflet of said valve;

an anchoring member coupled to said support member, said anchoring member including a compressed configuration and an expanded configuration;

wherein said expanded configuration of said anchoring member is shaped to position said support member at least partially within said valve.

BRIEF DESCRIPTION OF THE DRAWINGS

FIG. 6 illustrates a side view of the prosthesis of FIG. 5A within a heart;

FIGS. 7A and 7B illustrate a side view of the prosthesis of FIG. 5A within a delivery catheter;

FIGS. 8A and 8B illustrate a side view of the prosthesis of FIG. 5A with a retrieval thread;

FIG. 9A illustrates a front view of a prosthesis according to another preferred embodiment of the present invention;

FIG. 9B illustrates a side view of the prosthesis of FIG. 9A;

FIG. 11 illustrates a side view of the prosthesis of FIG. 10A during deployment from a delivery catheter;

FIG. 12A illustrates a front view of a prosthesis according to another preferred embodiment of the present invention;

FIG. 12B illustrates a side view of the prosthesis of FIG. 12A;

FIGS. 12C-12E illustrate various perspective views of the prosthesis of FIG. 12A;

FIGS. 16A and 16B illustrate side views of the prosthesis of FIG. 14A within a delivery catheter;

DETAILED DESCRIPTION OF THE INVENTION

Figure 1A:
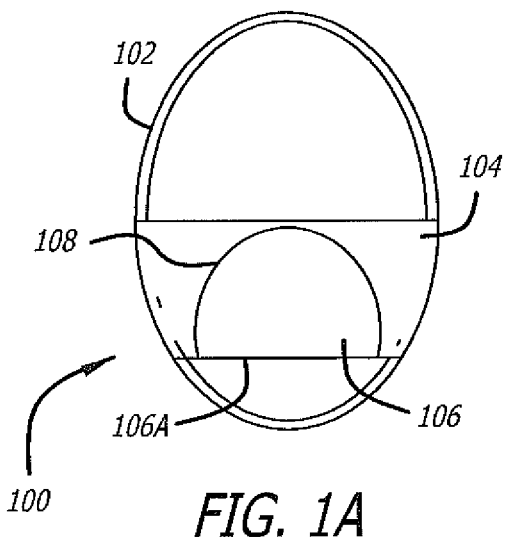
FIG. 1A illustrates a front view of a prosthesis according to one preferred embodiment of the present invention.
Figure 1B:
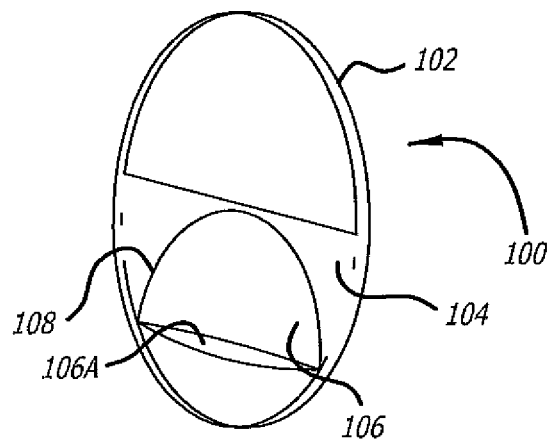
FIG. 1B illustrates a perspective view of the prosthesis of FIG. 1A.

The present invention seeks to reduce the amount of blood that flows into the left atrium from the left ventricle during the systole phase of heart contraction. Most instances of this mitral valve regurgitation are caused by poor coaptation of the mitral valve leaflets that create openings between these leaflets when the mitral valve is closed. The present invention decreases the size of these opening between the mitral valve leaflets, and in some cases completely eliminates the openings, allowing the mitral valve to function with little or no regurgitation. This is achieved in at least some of the example embodiments described in this specification by positioning a member between the two mitral valve leaflets to close or fill up the openings between the leaflets when closed.

FIGS. 1A-4

One such design can be seen in FIGS. 1A-4 which illustrates a preferred embodiment of a prosthesis 100 according to the present invention. The prosthesis 100 includes a pocket 106 formed from flexible material 104 disposed on a ring 102. As best seen in FIG. 1B, the pocket 106 includes a lower open end 106A that, when properly oriented within a mitral valve 120 of a heart 124, expands as the mitral valve 120 closes, blocking any openings between the mitral valve leaflets 122. Further, the pocket 106 contracts or deflates as the mitral valve 120 opens, maximizing blood flow from a left atrium 126 to a left ventricle 128. In this sense, the pocket 106 can more generally be described as an expandable occluding member or a coaptation member.

Figure 1C:
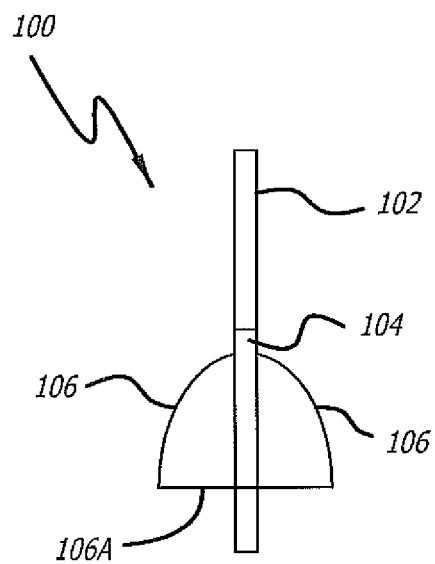
FIG. 1C illustrates a profile view of the prosthesis of FIG. 1A in an expanded configuration.
Figure 1D:
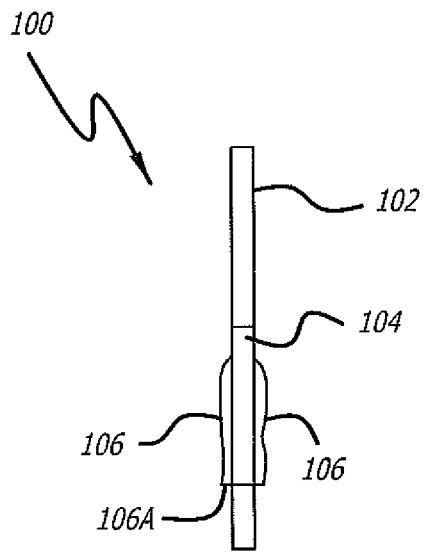
FIG. 1D illustrates a profile view of the prosthesis of FIG. 1A in a deflated configuration.
Figure 2A:
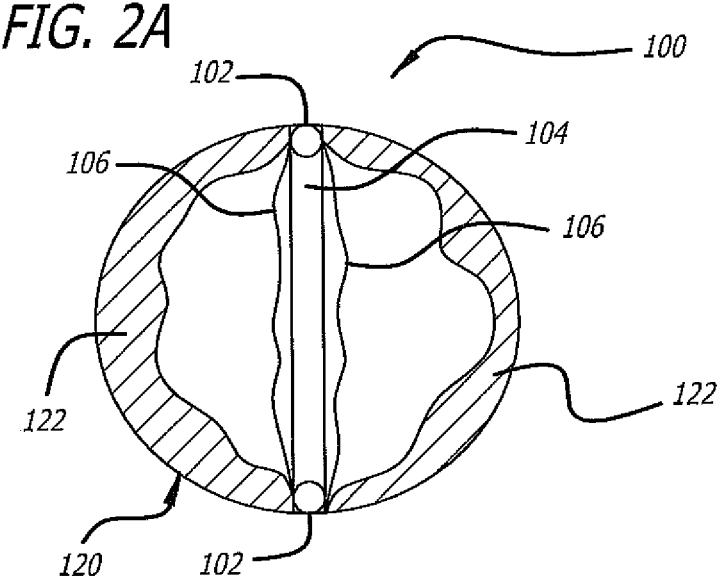
FIG. 2A illustrates a bottom view of the prosthesis of FIG. 1A in a deflated configuration within a mitral valve.
Figure 2B:
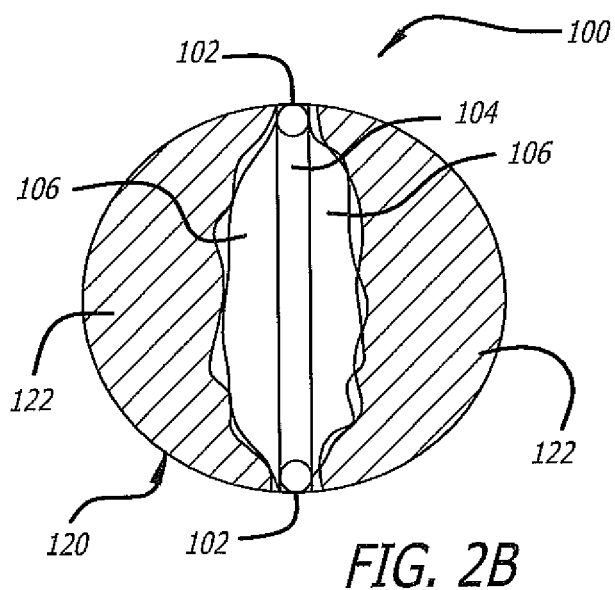
FIG. 2B illustrates a bottom view of the prosthesis of FIG. 1A in an expanded configuration within a mitral valve.

The pocket 106 is preferably created by gluing, stitching, or otherwise adhering at least two layers of the flexible material 104 at or around line 108. These layers can be achieved with two distinct pieces of material, or a single piece of material folded against itself. Preferably, the flexible material 104 is made from pericardial tissue or other biological or artificial materials with similar flexibilities, such as bovine tissue, polyurethane, or as described in U.S. Pat. No. 6,764,510, the contents of which are herein incorporated by reference. The shape of the pocket 106 and the flexibility of the flexible fabric 108 allow the pocket 106 to achieve a deflated position, as best seen in FIGS. 1D, 2A and 3A and an expanded position as best seen in FIGS. 1C, 2B and 3B.

While the pocket 106 can be shaped in a variety of different configurations, pocket shapes that facilitate entry and escape of blood from the pocket 106, such as the rounded arch-shape of pocket 106, are preferred. Configurations of the pocket 106 that include sharp corners or rough seams are less preferred due to their disruptive effect on blood flow into and out of the pocket 106. Preferably, the pocket 106 also includes an overall length similar to that of the mitral valve 120 and more preferably substantially the length of the mitral valve commissure, allowing the pocket 106 to fill any openings that may be present along the length of leaflets 122, as seen best in FIG. 2B. While a single pocket 106 is preferred, additional pockets or partitions within the pocket can also be included in the present invention.

Figure 4:
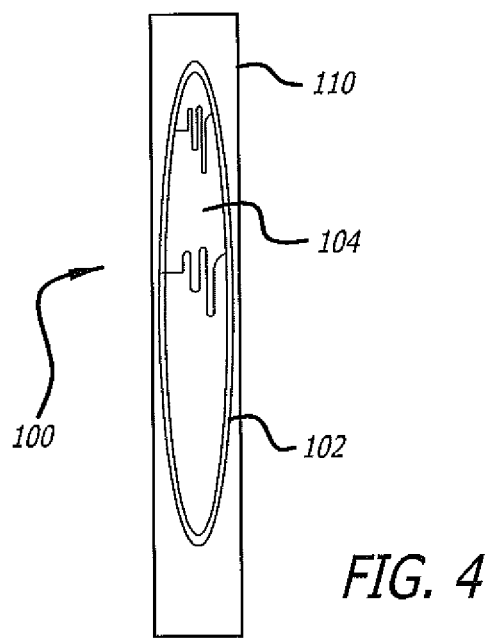
FIG. 4 illustrates a front view of the prosthesis of FIG. 1A in a delivery catheter.
Figure 3A:
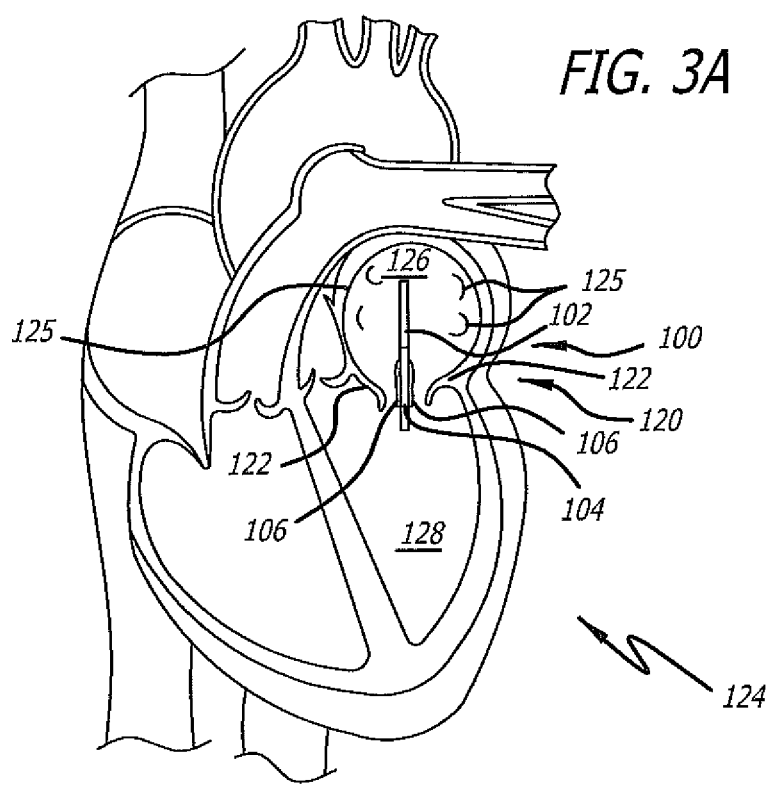
FIG. 3A illustrates a profile view of the prosthesis of FIG. 1A in a deflated configuration within a mitral valve.
Figure 3B:
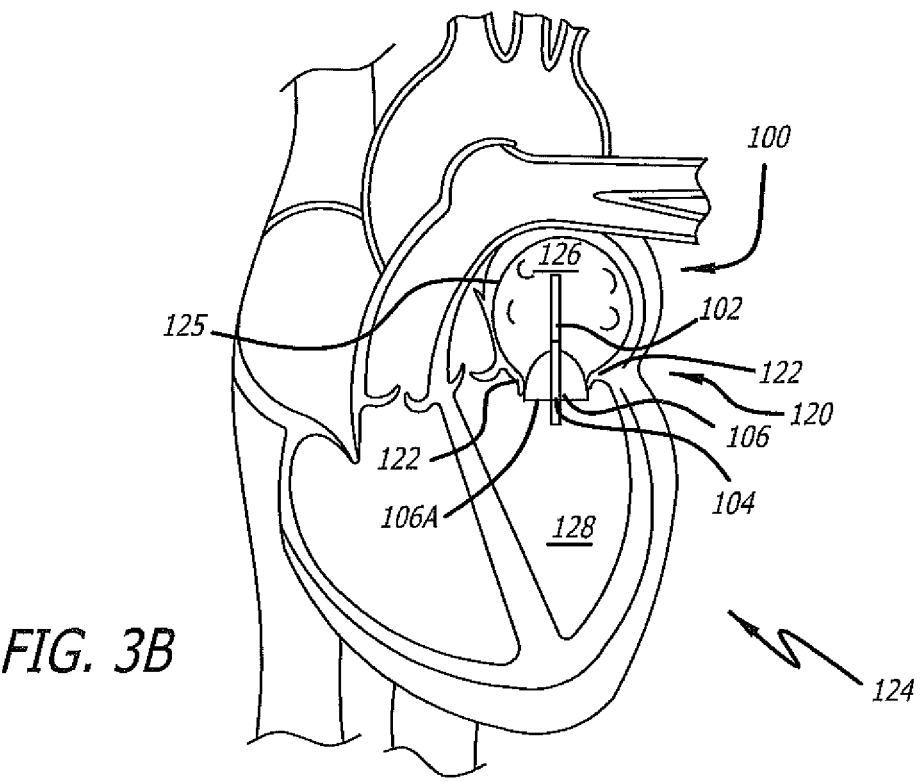
FIG. 3B illustrates a profile view of the prosthesis of FIG. 1A in an expanded configuration within a mitral valve.
Figure 5A:
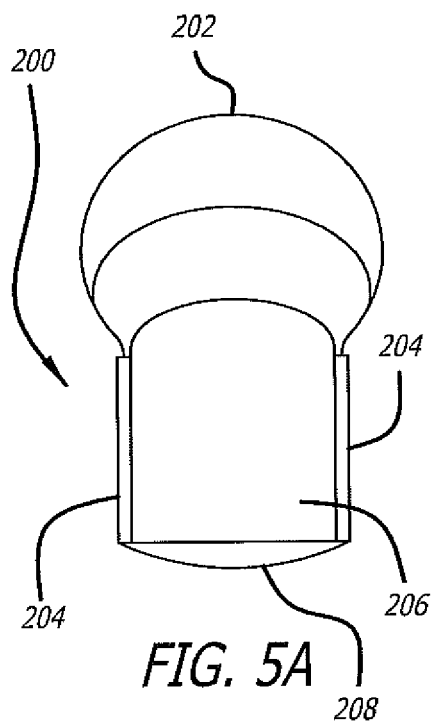
FIG. 5A illustrates a front view of a prosthesis according to another preferred embodiment of the present invention.
Figure 5B:
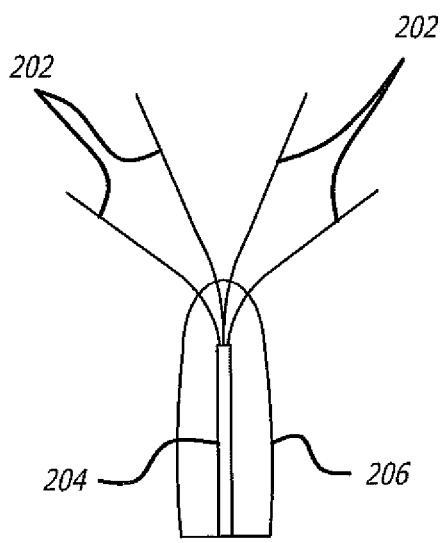
FIG. 5B illustrates a side view of the prosthesis of FIG. 5A.
Figure 5C:
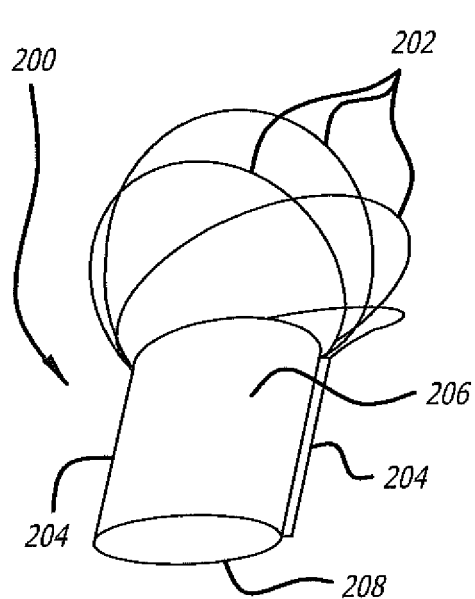
FIG. 5C illustrates a perspective view of the prosthesis of FIG. 5A.
Figure 5D:
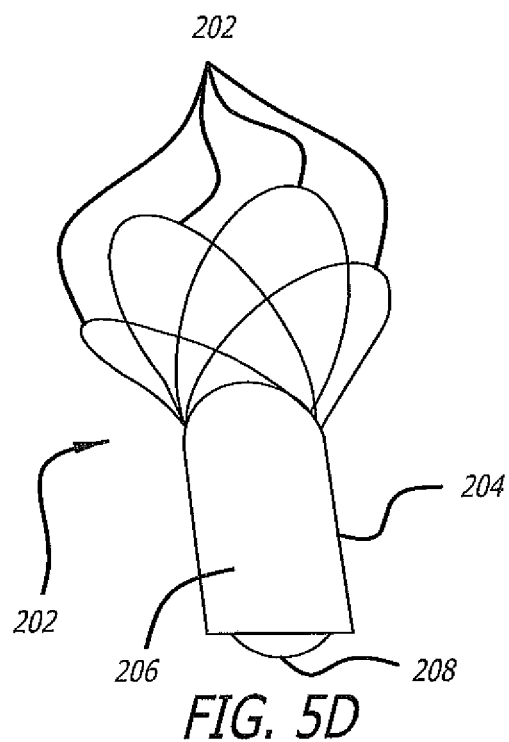
FIG. 5D illustrates a perspective view of the prosthesis of FIG. 5A.

The ring 102 is preferably made from an elastic, shape-memory material such as Nitinol which allows the prosthesis 100 to be compressed or loaded into a delivery catheter 110, as seen in FIG. 4, then expanded to a predetermined shape within the left atrium 126, as seen in FIGS. 3A and 3B. The ring 102 is sized to press against the walls of the left atrium 126 of the heart 124, and in some configurations within the commissure of the mitral valve 120, thereby anchoring the position of the prosthesis 100, while positioning the pocket 106 at least partially through a mitral valve 120. Additionally, the lower open end 106A of the pocket 106 is positioned near or within the left ventricle 128. In this sense, the ring 102 can more generally be described as an anchoring framework or an anchoring structure.

Once positioned within the heart 124, the prosthesis 100 functions in a similar manner to a heart valve, opening during diastole and closing during systole. More specifically, as blood enters the left atrium from the pulmonary veins 125 near the top of the left atrium 126, the blood flow moves downward towards the mitral valve 120. As the blood flow reaches the mitral valve 120, it pushes against the mitral valve leaflets 122 as the mitral valve 120 is opened by the papillary muscles. The blood flow also pushes against the pocket 106 of the prosthesis 100, forcing out any blood that may be within the pocket 106 and causing the pocket 106 to assume a substantially deflated or compressed position, as seen in FIG. 3A. This compressed configuration of the pocket 106 provides a streamline profile that minimizes blood flow resistance and other disruptive effects that a device within the left atrium might otherwise cause. In this respect, the blood flow during diastole passes into the left atrium 126, through the mitral valve 120 and past the prosthesis 100 to allow passage of the blood flow into the left ventricle 128.

During systole, backpressure from the blood in the left ventricle 128 presses against the mitral valve leaflets 122, as the papillary muscles move these leaflets 122 to a closed position. Additionally, this backpressure of blood in the left ventricle 128 enters the pocket 106 of the prosthesis 100, causing the pocket 106 to achieve an expanded shape, as seen in FIG. 3B. The mitral valve leaflets 124 coapt against the expanded pocket 106, as best seen in FIG. 2B, minimizing or even eliminating gaps that would otherwise be present between the two leaflets 122. Thus, blood flow during systole expands the prosthesis 100 to reduce or eliminate any openings that would otherwise be present between the leaflets 122, ultimately reducing or preventing regurgitation of blood into the left atrium 126.

Due in part to the dynamic, flexible nature of the pocket 106, the prosthesis 100 can expand to fill a wide range of opening sizes between the leaflets 122 without the need for an equally wide range of pocket sizes. In other words, the same size pocket 106 can expand to fill a relatively small opening or a relatively large opening between the mitral valve leaflets 122. Thus, the same size prosthesis 100 may be appropriate for a patient with relatively severe mitral valve regurgitation as well as relatively mild mitral valve regurgitation. Different sizes of prosthesis 100 may be appropriate, however, for different size mitral valves 120, since it is preferred that the pocket 106 extends along the length of the commissure of the mitral valve or the length of the "meeting line" between the two leaflets.

The prosthesis 100 is preferably delivered to the left atrium 126 percutaneously by a catheter 110, as seen in FIG. 4. For example, the delivery catheter 110 may be fed through the femoral vein, into the right atrium and passed through a pre-made puncture in the atrial septum 125. In another example, the delivery catheter 110 can be passed through the femoral artery into the aorta, through the aortic valve and into the left ventricle.

Alternately, the prosthesis 100 can be inserted into the left atrium 126 through an opening in the atrial wall of the heart 125 during open-heart surgery. Although the prosthesis 100 can be seen and positioned more easily during open-heart procedures, percutaneous delivery is less invasive and therefore includes a substantially lower risk of complications. FIGS. 5A-8B Another preferred embodiment of a prosthesis 200 according to the present invention can be seen in FIGS. 5A-7B. While generally similar to the prosthesis 100, the prosthesis 200 also includes four anchoring loops 202 that expand to anchor the prosthesis 200 within the left atrium 126 and position a pocket 206 between the mitral valve leaflets 122, along the length of the mitral valve commissure. In this respect, the anchoring loops 202 can more generally be described as an anchoring framework or an anchoring structure.

The pocket 206 is supported by support arms 204 and bottom support 208 which provide a support framework for the pocket 206. Preferably the side arms 204 and the bottom support 208 are a single, unitary wire that connect to the anchoring loops 202, however multiple segments of wire can be connected together, for example by welding or soldering, as well. As with the previously described embodiment of the prosthesis 100, the support arms 204 and the bottom support 208 are preferably composed of an elastic, memory-shape material, such as Nitinol, which allows the prosthesis 200 to be compressed and loaded into a catheter 110, as seen in FIGS. 7A and 7B, then deployed to the predetermined shape seen in FIGS. 5A-6. Preferably, the wires used for the support arms 204 and the bottom support 208 are sized and shaped to cause minimal deformation of the free edges of the leaflets 122, and therefore minimize distortion of the mitral valve geometry. In this respect, the pocket support arms 204 can alternatively be described as a framework, a support structure, or a positioning frame.

The pocket 206 is similar to the pocket 106 of the previous embodiment, preferably being composed of a flexible biological or artificial material that is sized and shaped to form a pocket-shape with an opening directed opposite to the anchoring loops 202. The pocket 206 can be directly stitched, glued, or adhered to the outer support arms 204 for support. Alternately, the flexible fabric of the pocket 206 can be stitched to form an elongated passage for the support arms 204 on the outer surface of the pocket 206.

As best seen in FIG. 6, the pocket 206 is positioned at least partially within the mitral valve 120 so that the open end of the pocket 206 is faced toward the left ventricle 128. In this configuration, the pocket 206 is deflated during diastole, minimizing blood flow blockage in the mitral valve 120, and expanded during systole, at least partially filling any openings between the mitral valve leaflets 122 and thereby minimizing blood flow regurgitation into the left atrium 126.

The prosthesis 200 is preferably delivered to the left atrium 126 by a percutaneous delivery catheter 110 but can also be implanted during open-heart surgery, as described in regards to the prosthesis 100. Since the pocket 206 has a horizontally elongated shape that requires a specific orientation within the mitral valve 120, percutaneous delivery of the prosthesis 200 to the proper position may be more difficult than delivery during open-heart surgery. Accordingly, the delivery catheter 110 may include a retrieval thread 210 and a push rod 212 as seen in FIGS. 8A and 8b to retrieve the prosthesis 200 back into the catheter 110 and redeploy the prosthesis 200 at a new position within the left atrium 126.

Preferably, the retrieval thread 210 is composed of a thin but strong material such as metal, silk, or polypropylene, and is a single segment. Both free ends of the retrieval thread 210 are positioned at a proximal end of the delivery catheter 110, while the body of the thread 210 extends through the deliver catheter 110, through each anchoring loop 202 and back through the catheter 110.

Depending on the configuration of the prosthesis 200 in an expanded state, the retrieval thread 210 alone may not provide the necessary force to fully recompress and recapture the prosthesis 200. In such situations, the pusher rod 212 may be used in conjunction with the retrieval thread 210 to manipulate the prosthesis 200 into a shape acceptable for recapture within the delivery catheter 110. For example, the operator of the delivery catheter 110 may pull on the retrieval thread 210 while pushing on the anchoring loops 202 with the pusher rod 212. The simultaneous pushing and pulling deform the anchoring loops 202 into an elongated shape that can more easily be recaptured by the delivery catheter 110, allow the user to reposition the distal end of the delivery catheter 110 and redeploy the prosthesis 200.

FIGS. 9A-9E

Figure 9C:
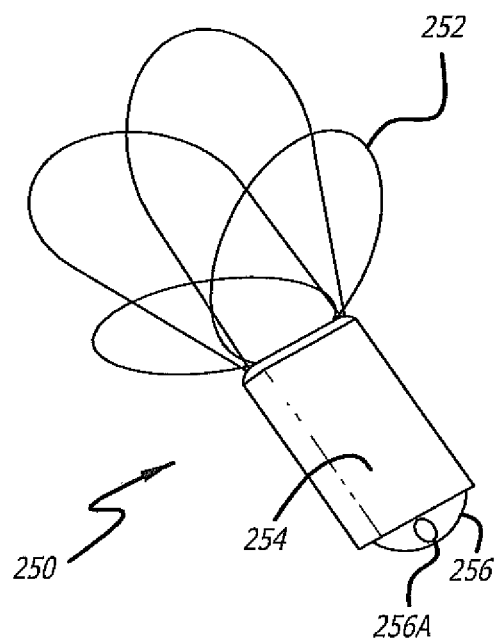
FIG. 9C illustrates a perspective view of the prosthesis of FIG. 9A.
Figure 9D:
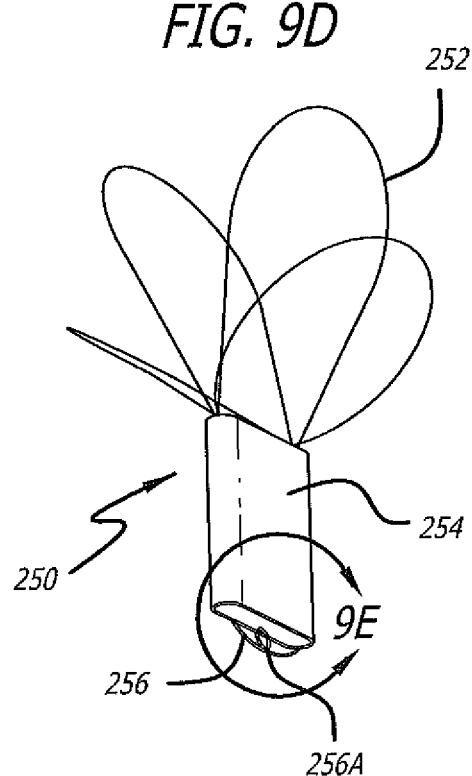
FIG. 9D illustrates a perspective view of the prosthesis of FIG. 9A.
Figure 9E:
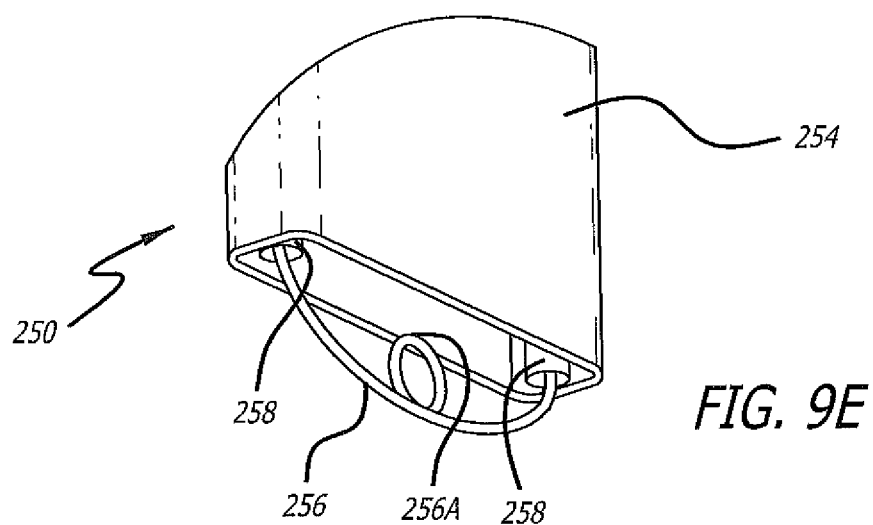
FIG. 9E illustrates an enlarged view of area 9E in FIG. 9D.

FIGS. 9A-9E illustrate another preferred embodiment of a prosthesis 250 that is mostly similar to the prosthesis 200 previously shown in FIGS. 5A-8B, having anchoring loops 252 fixed to support arms 258 and a pocket 254 disposed between the support arms 256. However, as best seen in FIG. 9E, the support arms 258 of the present prosthesis 250 are positioned and attached within the pocket 254 instead of on the outer surface of the pocket 254, creating a more uniform outer surface shape compared with the prosthesis 200. Additionally, the bottom support 256 includes a loop 256A that is configured to exert force against the support arms 258 to maintain the pocket 254 in a fully expanded position.

FIGS. 10A-11

Figure 10A:
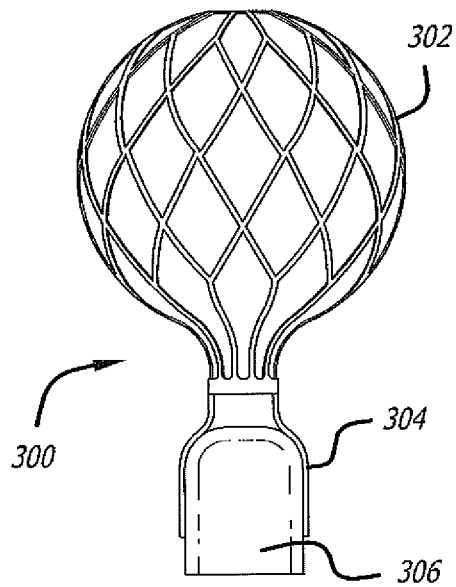
FIG. 10A illustrates a front view of a prosthesis according to another preferred embodiment of the present invention.
Figure 10B:
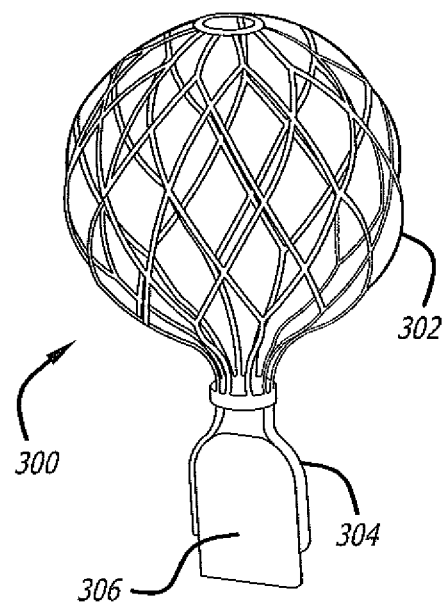
FIGS. 10B-10D illustrate various perspective views of the prosthesis of FIG. 10A.
Figure 10C:
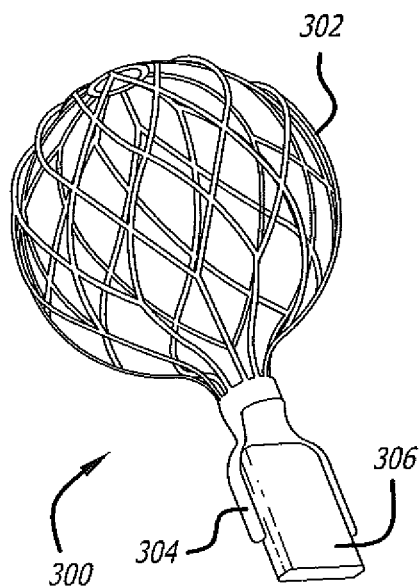
Figure 10D:
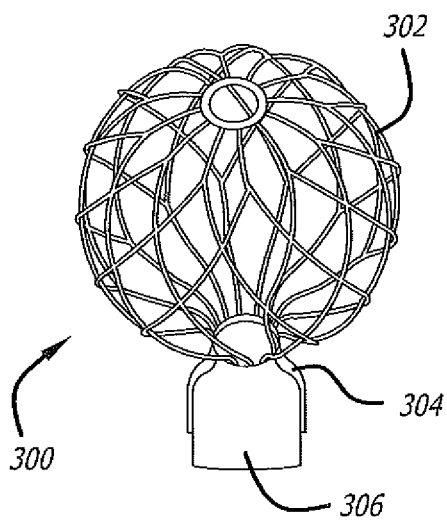

FIGS. 10A-11 illustrate yet another embodiment of a prosthesis 300 according to the present invention that is generally similar to the previously described embodiments of this specification, having support arms 304 that support a pocket 306 made from flexible material.

Unlike the embodiments previously described in this specification, the prosthesis 300 includes an anchoring cage 302 that is unitary with the support arms 304. Preferably, both the anchoring cage 302 and the support arms 304 are cut from a single metal tube, such as by laser cutting the desired pattern into the tube or by other techniques used to manufacture stents. The metal of the tube is preferably composed a shape memory material, such as those commonly used for stents such as Nitinol. In this regard, the anchoring cage 302 can more generally be described as an anchoring framework or an anchoring structure.

Once expanded within the left atrium 126, the anchoring cage 302 contacts the tissue of the left atrium 126 in more positions that embodiments previously described in this specification and therefore more uniformly distributes the anchoring force within the left atrium 126. Additionally, the expanded shape of the anchoring cage 302 can be shaped to better conform to the geometry of the left atrium 126 and therefore more precisely position the pocket 306 at a desired location.

As with the previously described embodiments of this specification, the prosthesis 300 is preferably delivered percutaneously with a delivery catheter 110 as seen in FIG. 11, but may alternately be deployed during open-heart surgery. In the case of percutaneous deployment, the prosthesis 300 compresses to a relatively small pre-deployed state, as seen in FIG. 11.

FIGS. 12A-13

Figure 13:
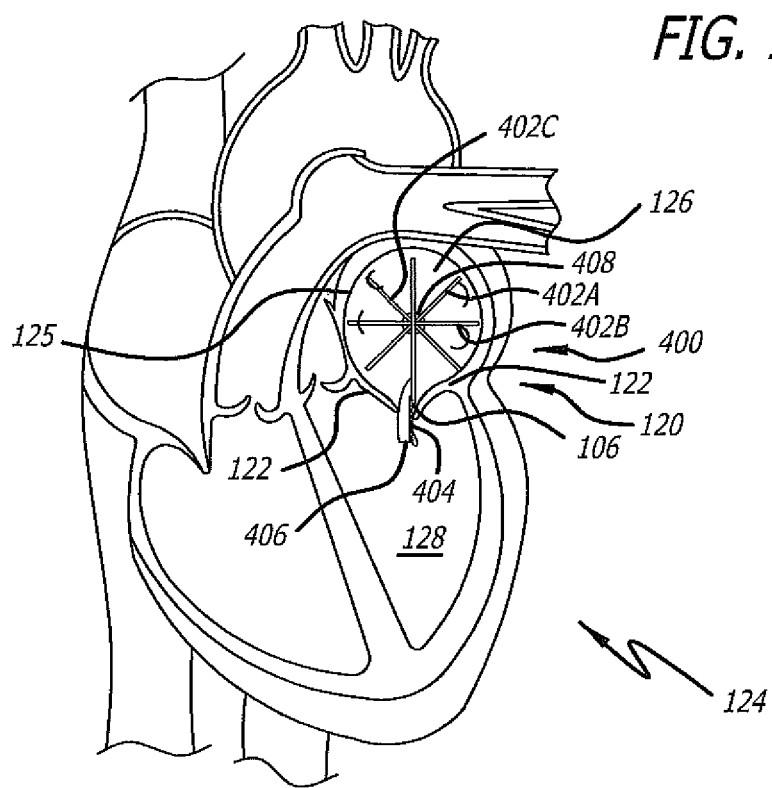
FIG. 13 illustrates a side view of the prosthesis of FIG. 12A within a heart.
Figure 15:
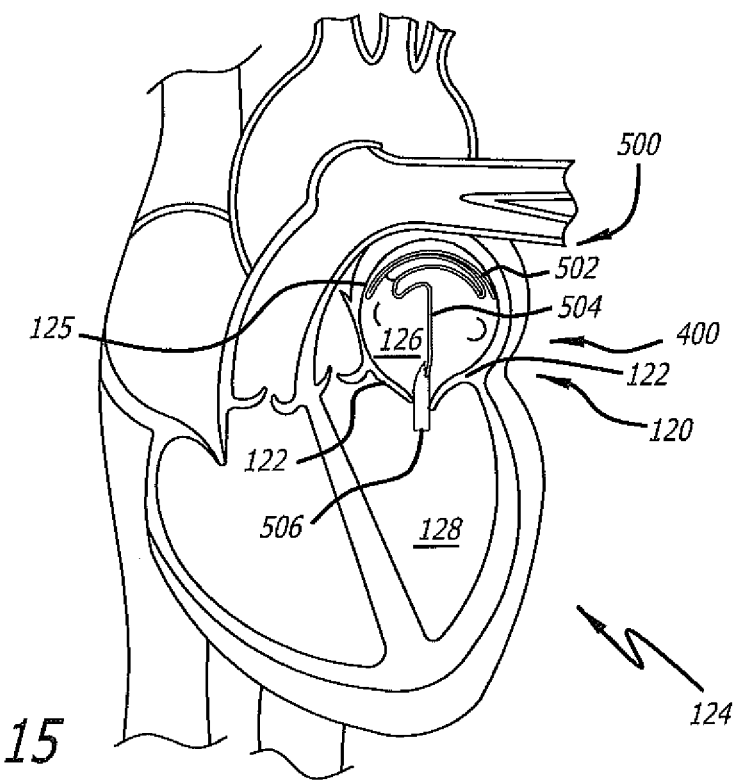
FIG. 15 illustrates a side view of the prosthesis of FIG. 14A within a heart.
Figure 14A:
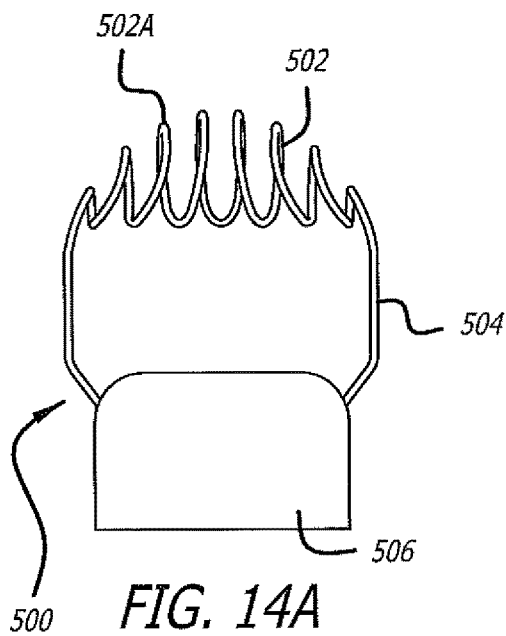
FIG. 14A illustrates a front view of a prosthesis according to another preferred embodiment of the present invention.
Figure 14B:
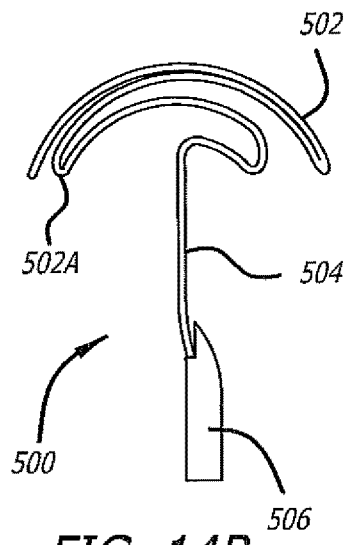
FIG. 14B illustrates a side view of the prosthesis of FIG. 14A.
Figure 14C:
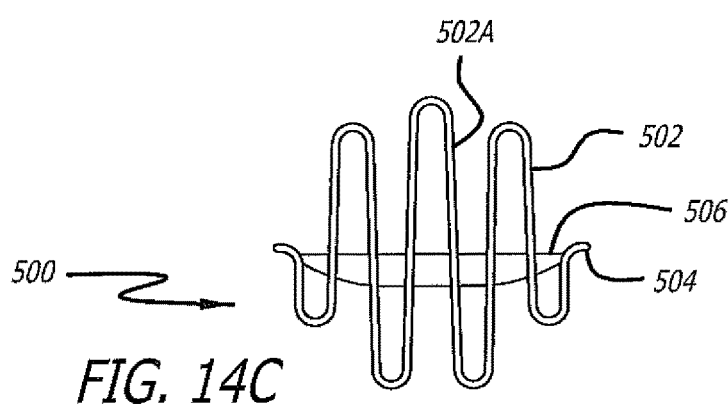
FIG. 14C illustrates a top view of the prosthesis of FIG. 14A.
Figure 14D:
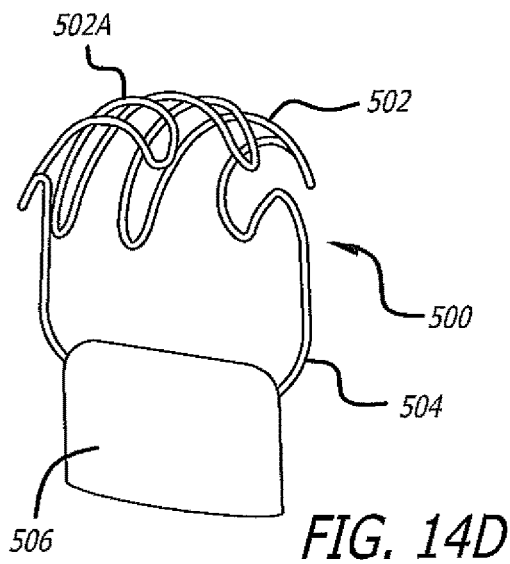
FIGS. 14D and 14E illustrate various perspective views of the prosthesis of FIG. 14A.
Figure 14E:
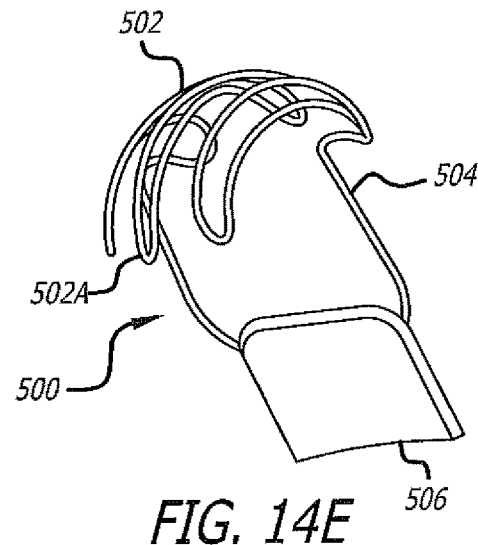
Figure 17A:
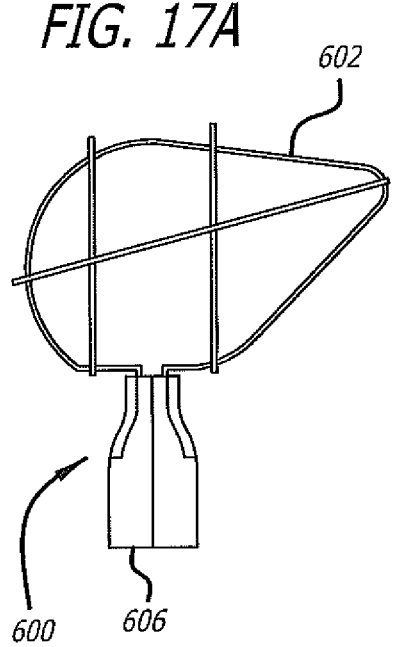
FIG. 17A illustrates a front view of a prosthesis according to another preferred embodiment of the present invention.
Figure 17B:
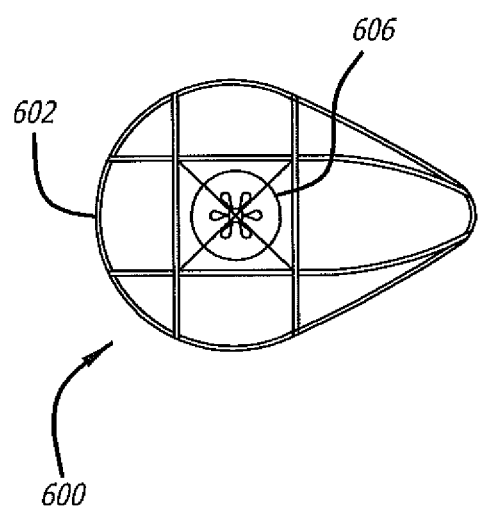
FIG. 17B illustrates a top view of the prosthesis of FIG. 17A.
Figure 17C:
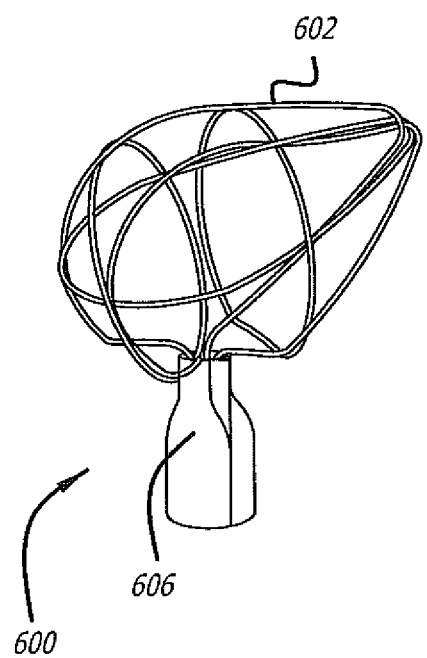
FIGS. 17C and 17D illustrate perspective views of the prosthesis of FIG. 17A.
Figure 17D:
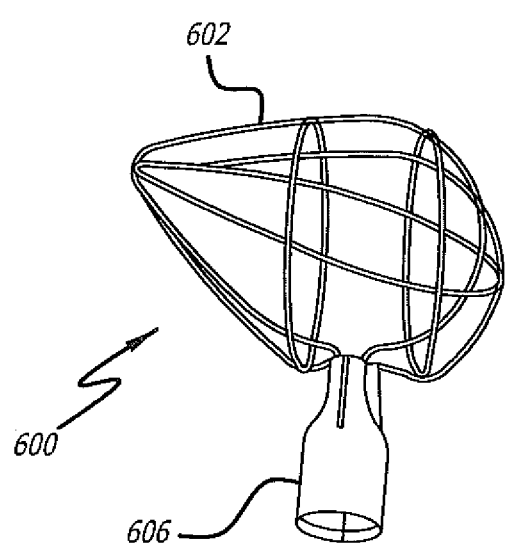

FIGS. 12A-13 illustrate another preferred embodiment of a prosthesis 400 according to the present invention, which is generally similar to the previously described embodiments, such as the prosthesis 200 shown in FIGS. 5A-8B. More specifically, the similarities of the prosthesis 400 include anchoring loops 402 that anchor and position a pocket 406 via support arms 404. The pocket 406 is similarly positioned within the mitral valve 120 so as to expand into any openings between the mitral valve leaflets 122 when the mitral valve 120 is closed.

In contrast to the previously described embodiments, the prosthesis 400 includes multiple anchoring loops 402 that form a spherical, lemon shape having a terminating region 408. The overall shape of the anchoring loops 402 expand to apply pressure against the left atrium 126 at different angles which better maintains the position of the prosthesis 400. Additionally, the terminating region 408 can press against the tissue of the left atrium 126 or can alternatively be positioned within an incision within the wall of the left atrium 126 (e.g., a percutaneous access incision within the atrium septum) to provide further anchoring support.

The body of the prosthesis 400 includes wires 402A-402E that are shaped to form the anchoring loops 402, as well as two pocket supports 404. Wires 402B, 402C, and 402D are shaped to have a generally circular shape with each of the free ends captured by terminating region 408. In this respect, each wire 402B, 402C, and 402D forms a single loop of the prosthesis 400.

One end of wire 402A is fixed within terminating region 408 while the other end extends down to form a pocket support 404, including an arch-shape in between the two ends having a similar shape to those formed by wires 402B, 402C, and 402D. The second pocket support 404 is formed from wire 404E which is similarly fixed within terminating region 408. As with the previously described embodiments described in this specification, the pocket 406 is fixed to the pocket supports 404, thereby maintaining the pocket 406 at a desired location within the mitral valve 120, as best seen in FIG. 13. In this regard, the anchoring loops 402 can more generally be described as an anchoring framework or an anchoring structure.

FIGS. 14A-16B

In another preferred embodiment illustrated in FIGS. 14A-16B, a prosthesis 500 is shown according to the present invention. Similar to previous embodiments discussed within this specification, the prosthesis 500 includes a pocket 506 that is supported and positioned by an anchoring wire 502. While the present prosthesis 500 includes curved anchoring regions 502A, similar to the curved anchoring wires of previously discussed embodiments, these anchoring regions 502A are composed of a single anchoring wire 502. By using a single anchoring wire 502, the prosthesis 500 minimizes the possible sharp ends or edges that may otherwise be present. In this sense, the anchoring wire 502 can more generally be described as an anchoring framework or an anchoring structure.

As seen in FIGS. 16A and 16B, one possible delivery method of the prosthesis 500 includes compressing or loading the prosthesis 500 within the percutaneous delivery catheter 110 and delivering the prosthesis 500 to the left atrium 126. Once within the left atrium 126, the prosthesis 500 expands to the predefined shape seen in FIG. 15. Thus, the prosthesis 500 maintains the position of the pocket 506 within the mitral valve 120, similar to previously discussed embodiments, reducing regurgitation.

FIGS. 17A-17D

FIGS. 17A-17D illustrate yet another preferred embodiment of a prosthesis 600 according to the present invention that reduces mitral valve regurgitation similar to the embodiments previously described in this specification by anchoring a pocket 606 within the mitral valve 120.

In contrast, present prosthesis 600 includes anchoring wires 602 shaped to have an asymmetrical egg structure that more closely resembles the asymmetrical interior of the left atrium 126. Since the asymmetry of the anchoring wires 602 matches the natural asymmetry of the left atrium 126, the prosthesis 600 expands and orients itself in a predetermined position, providing stable anchoring and consistent alignment of the pocket 606 with the mitral valve 120. Further, this asymmetrical design facilitates delivery and deployment from the position of an incision through the atrial septum, since the prosthesis 600 expands to firmly engage the geometry of the left atrium 126. In this regard, the anchoring wires 602 can more generally be described as an anchoring framework or an anchoring structure.

The pocket 606 also includes a radial or cylinder shape when fully expanded, and can more generally be described as an expandable occluding member or a coaptation member. The radial shape imparts a uniform hydraulic function that is similar, regardless of the rotationally orientation of the pocket 606 relative to the mitral valve leaflets 122 (i.e., the commissure of the mitral valve 120). In this respect, the prosthesis 600 can be deployed to a greater number of orientations without adversely affecting the reduction of regurgitation.

FIGS. 18A-18D

FIGS. 18A-18D show another preferred embodiment of a prosthesis 700 according to the present invention that is much like the previously described prosthesis 600, having anchoring wires 702 forming an asymmetrical shape similar to the geometry of the left atrium 126. However, the present prosthesis 700 includes a pocket 706 with an elongated, non-radial shape that is coupled to the anchoring wires 702 by a rotating swivel 710. The swivel 710 allows rotation between the pocket 706 and the anchoring wires 702, allowing the pocket 706 to achieve a desired rotational orientation within the mitral valve 120, regardless of the orientation of the anchoring wires 702. In this respect, the anchoring wires 702 can more generally be described as an anchoring framework or an anchoring structure.

Figure 18A:
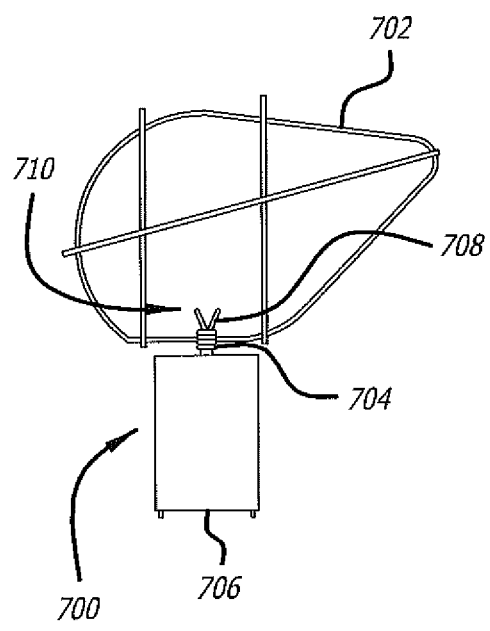
FIG. 18A illustrates a front view of a prosthesis according to another preferred embodiment of the present invention.
Figure 18B:
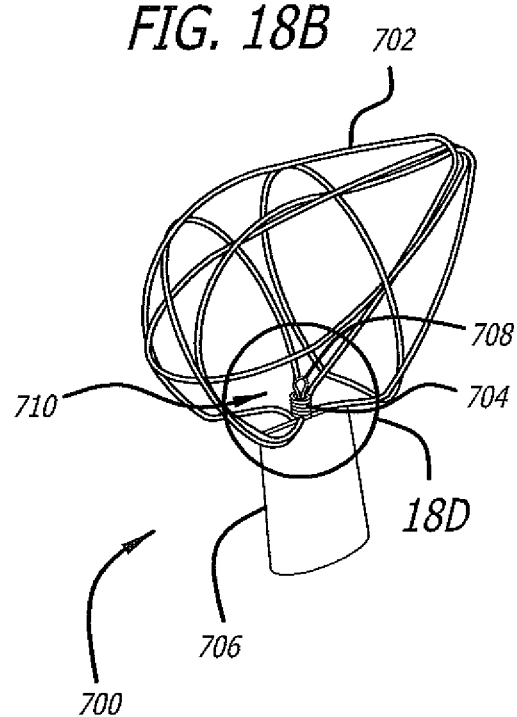
FIGS. 18B and 18C illustrate various perspective views of the prosthesis of FIG. 18A.
Figure 18C:
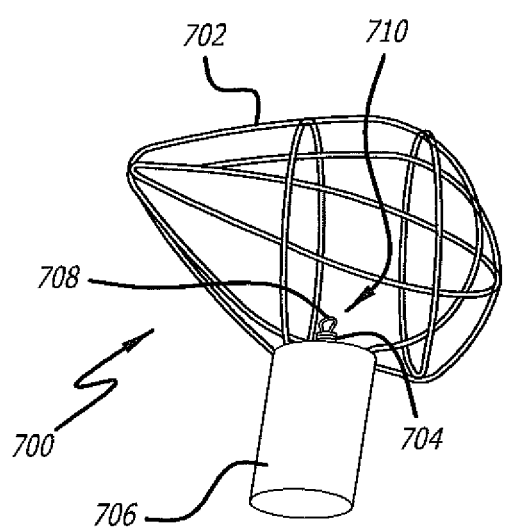
Figure 18D:
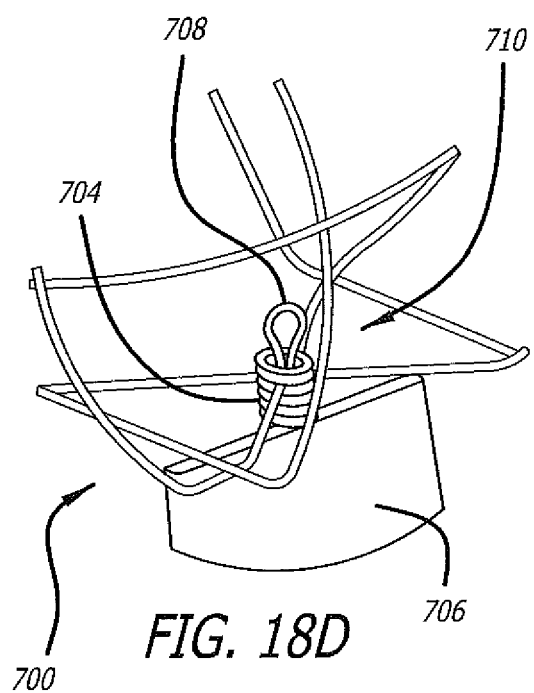
FIG. 18D illustrates an enlarged view or area 18D in FIG. 18B.

As best seen in FIG. 18D, the swivel 710 is composed of wire loop 708 that extends from an unseen wire support of the pocket 706. The anchoring wires 702 include a wire coil 704 that encircles and thereby engages the wire loop 708, allowing the anchoring wires 702 to rotate in relation to the pocket 706. In this respect, the surgeon can more easily deploy the prosthesis 700 percutaneously by first positioning the pocket 706 at a desired position within the mitral valve 120, then deploying the anchoring wires 702 without the need to adjust the overall rotational orientation of the prosthesis 700. Additionally, the ability of the prosthesis 700 to rotate allows the pocket 706 to self align so that each mitral valve leaflet 122 contacts against an elongated side of the pocket 706.

FIGS. 19A-19D

FIGS. 19A-19D illustrate a preferred embodiment of a prosthesis 800 that is similar to the embodiments previously described in this specification, especially the prosthesis 700 shown in FIGS. 18A-18D. More specifically, the prosthesis 800 includes anchoring wires 802 which expand to an asymmetrical shape, similar to the geometry of the left atrium 126. Additionally, the prosthesis 800 includes an elongated pocket 806 coupled to the anchoring wires 802 by a rotating joint 810. In this regard, the anchoring wires 802 can more generally be described as an anchoring framework or an anchoring structure.

Figure 19A:
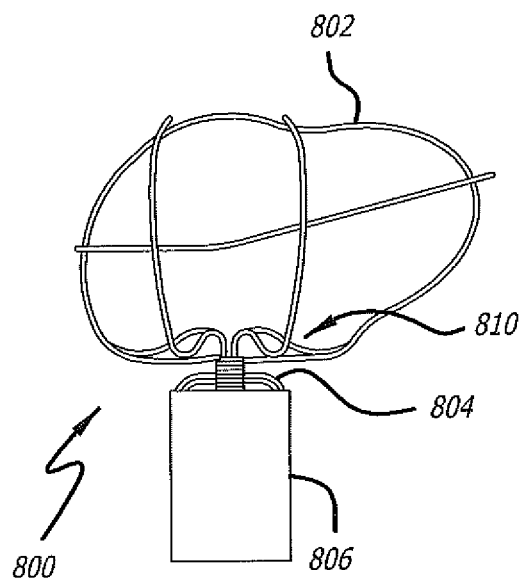
FIG. 19A illustrates a front view of a prosthesis according to another preferred embodiment of the present invention.
Figure 19B:
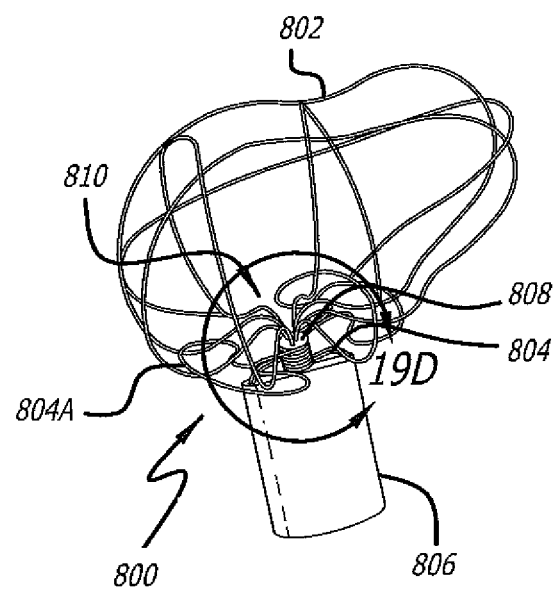
FIGS. 19B and 19C illustrate various perspective views of the prosthesis of FIG. 19A.
Figure 19C:
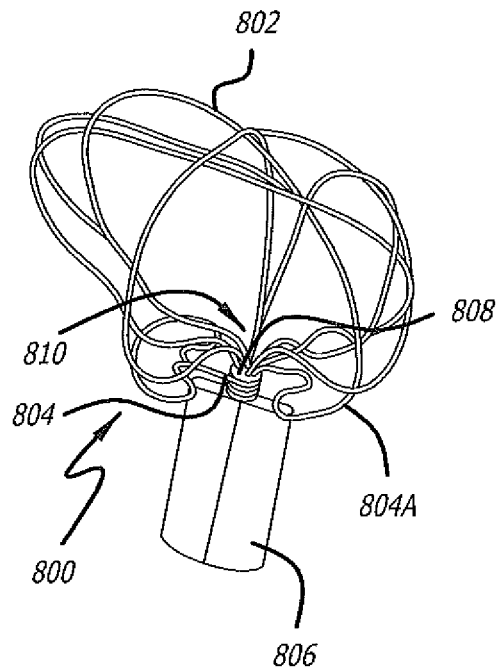
Figure 19D:
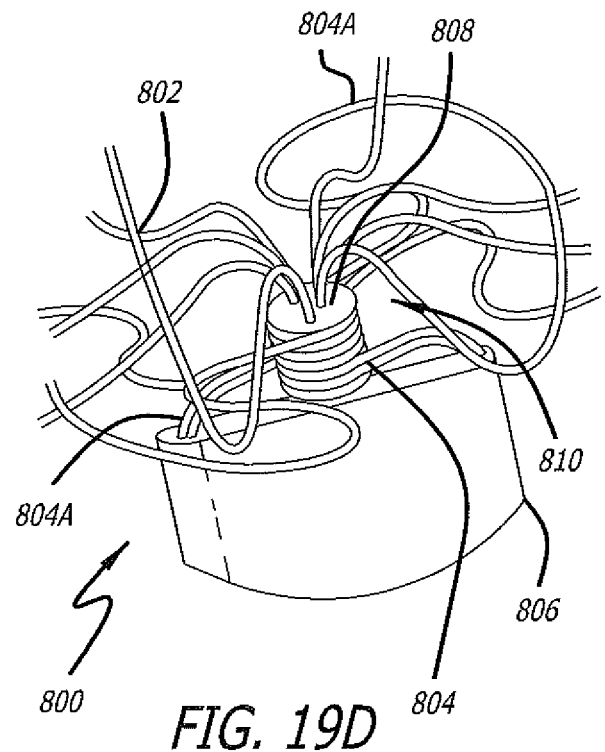
FIG. 19D illustrates an enlarged view or area 19D in FIG. 19B.
Figure 20A:
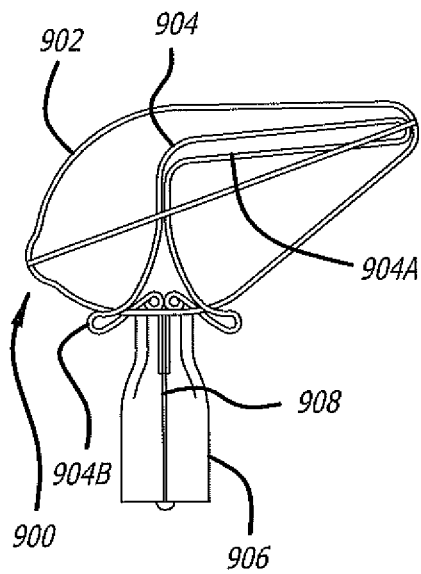
FIG. 20A illustrates a front view of a prosthesis according to another preferred embodiment of the present invention.
Figure 20B:
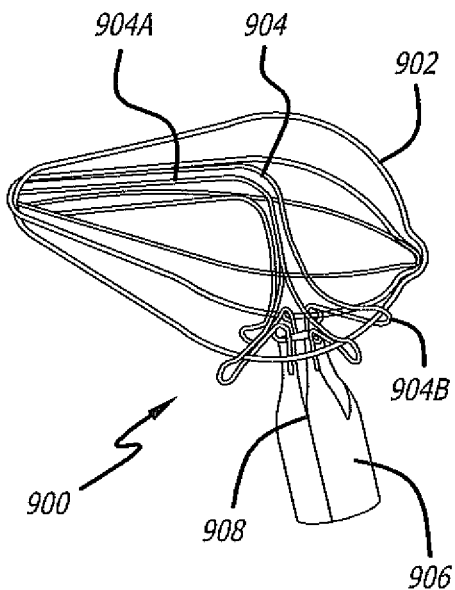
FIGS. 20B and 20C illustrate various perspective views of the prosthesis of FIG. 20A.
Figure 20C:
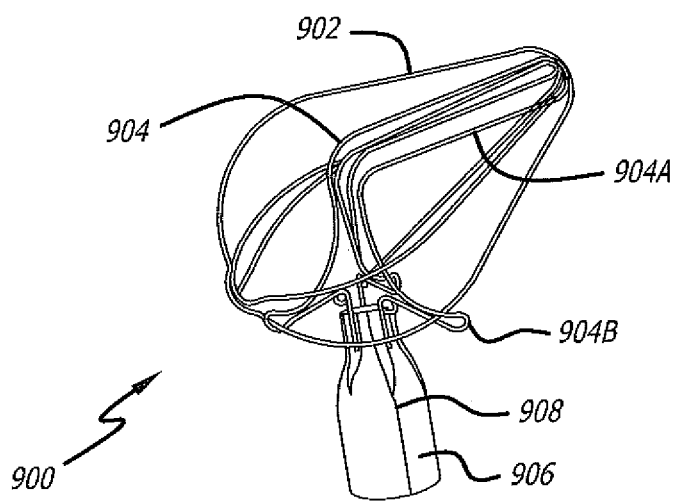

In contrast to the previously described prosthesis 700, the prosthesis 800 includes a pocket support wire 804 that not only supports the structure of the pocket 806, as described in other embodiments in this specification, but also wraps around a cylinder 808, then branches radially outward into loop shapes 804A, as best seen in FIG. 19D. The ends of anchoring wires 802 are coupled within the cylinder 808 so as to allow the anchoring wires 806 rotate freely from the pocket 806.

The looped regions 804A of the pocket support wire 804 assist the freely rotating pocket 806 in orienting itself to a desired position within the mitral valve 120. Additionally, these outer looped regions 804A can be sized and shaped to provide support to the pocket 806 by resting on the annulus of the mitral valve 120.

Alternately, the looped regions of the pocket support wire 804 can be shaped to at least partially interlock with a portion of the anchoring wires 802 to allow the anchoring wires 802 to freely rotate within a range, determined and therefore restricted by the length of the loops of the pocket support wire 804. Such a rotational restriction may better assist the surgeon in delivering and deploying by allowing at least some degree of rotational control over the pocket 806 in a deployed configuration.

FIGS. 20A-21B

FIGS. 20A-21B illustrate yet another preferred embodiment of a prosthesis 900 according to the present invention which is generally similar to the previously discussed embodiments of this specification, such as prosthesis 600 of FIGS. 17A-17D. For example, the prosthesis 900 includes a pocket 906 having a radial shape and pocket support wires 908, as well as anchoring wires 902 fixed to the pocket 906 and having an asymmetrical shape generally matching the inner geometry of the left atrium 126.

However, the prosthesis 900 includes two separately deployable support structures: the previously mentioned anchoring wires 902 and inner support wires 904. The inner support wires 904 include elongated region 904A and anchoring region 904B which continues within the pocket 906 as support wires 908. The anchoring wires 902 and inner support wires 904 can more generally be described as an anchoring framework or an anchoring structure.

Figure 21A:
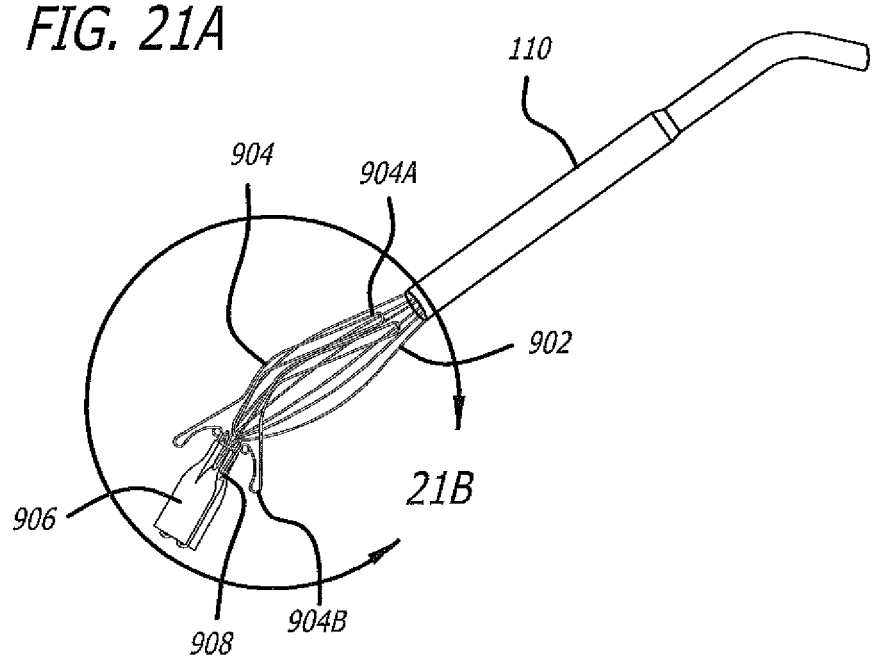
FIG. 21A illustrates a side view of the prosthesis of FIG. 20A in a partially deployed configuration.
Figure 21B:
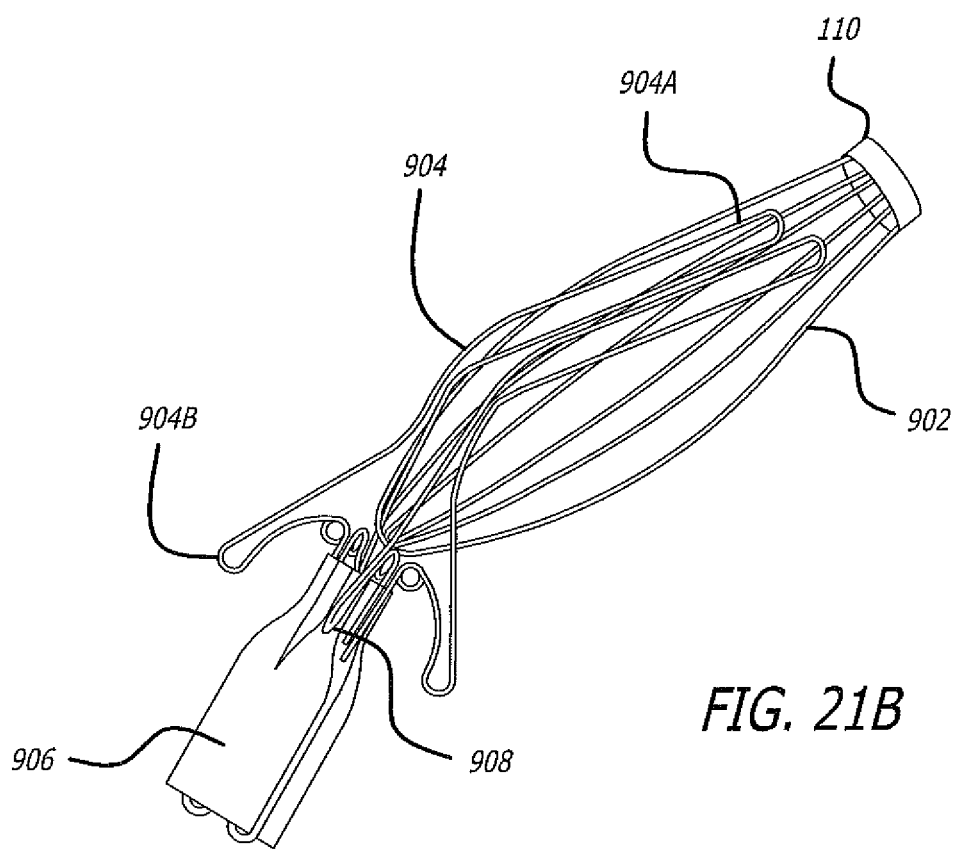
FIG. 21B illustrates an enlarged view of area 21B in FIG. 21A.

As best seen in FIGS. 21A and 21B, the support structures 902 and 904 can be deployed separately during a percutaneous deliver with the deliver catheter 110. As the prosthesis 900 is pushed out of the delivery catheter 110, the inner support wire 904, including elongated region 904A and anchoring region 904B, expand first while the anchoring wires 902 remain relatively compressed.

The expanded shape of the anchoring region 904B is preferably sized and shaped to engage at least a portion of the annulus of the mitral valve 120. In this respect, the user can direct the pocket 906 to a desired position within the mitral valve 120 while the anchoring region 904B expands to at least partially anchor the pocket 906 in place. Once the user has achieved a desired position for the pocket 906, the remaining anchoring wires 902 can be deployed from the delivery catheter 110, allowing them to expand to press against the left ventricle 126, thereby further anchoring the prosthesis 900 in place.

FIGS. 22A-22C

Figure 22A:
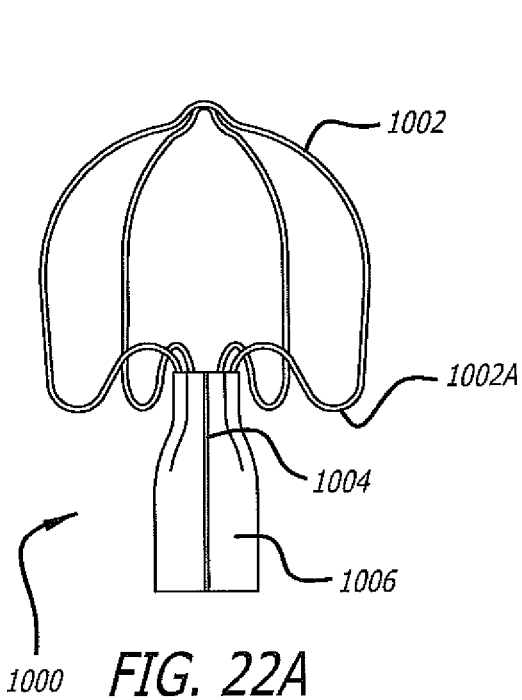
FIG. 22A illustrates a front view of a prosthesis according to another preferred embodiment of the present invention.
Figure 22B:
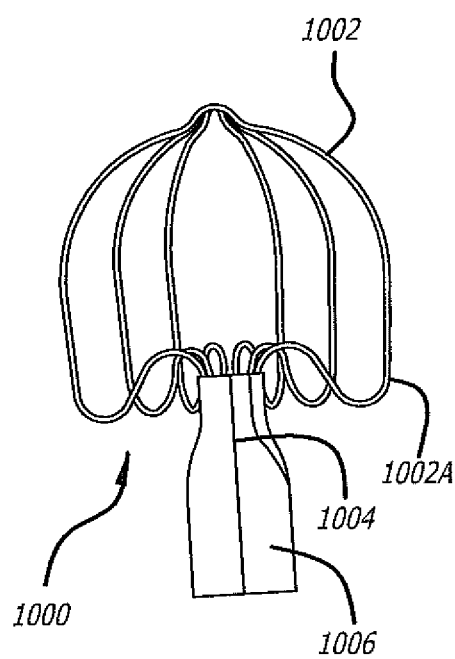
FIGS. 22B and 22C illustrate various perspective views of the prosthesis of FIG. 22A.
Figure 22C:
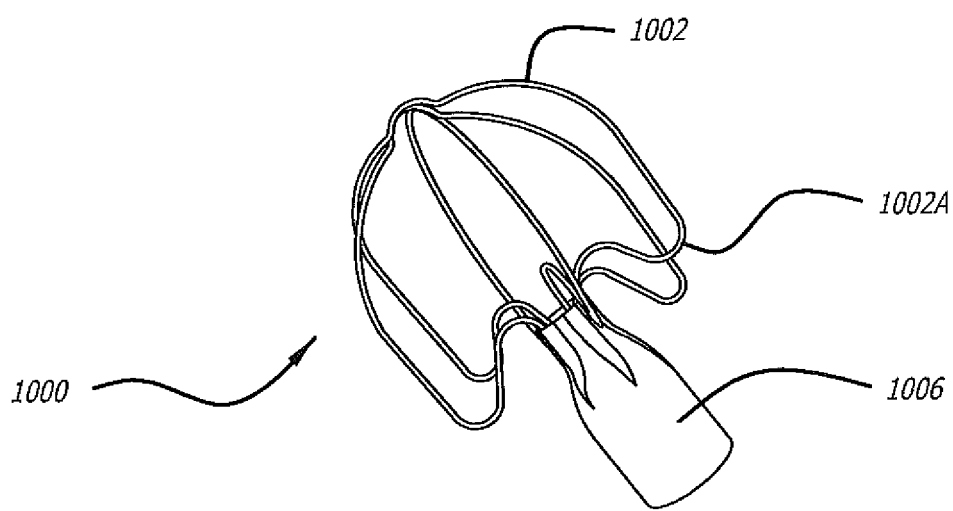
Figure 23A:
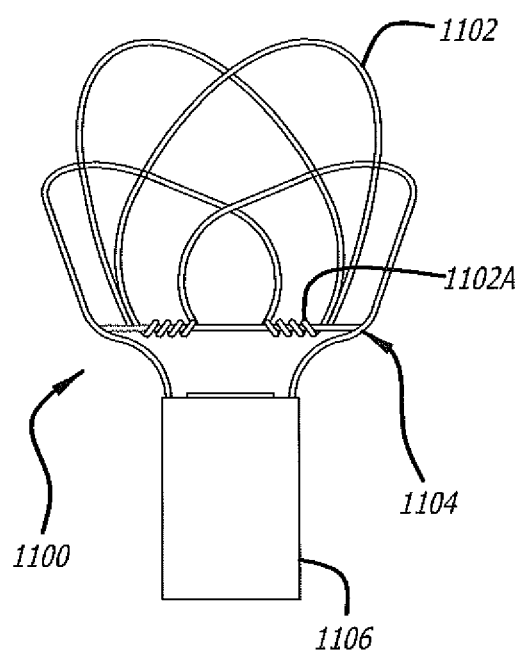
FIG. 23A illustrates a front view of a prosthesis according to another preferred embodiment of the present invention.
Figure 23B:
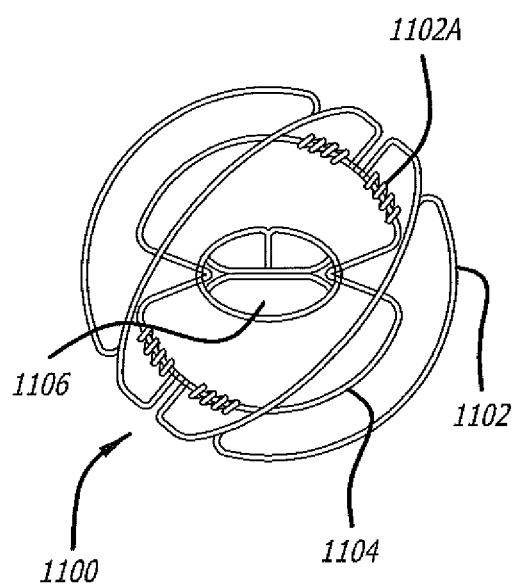
FIG. 23B illustrates a top view of the prosthesis of FIG. 23A.
Figure 23C:
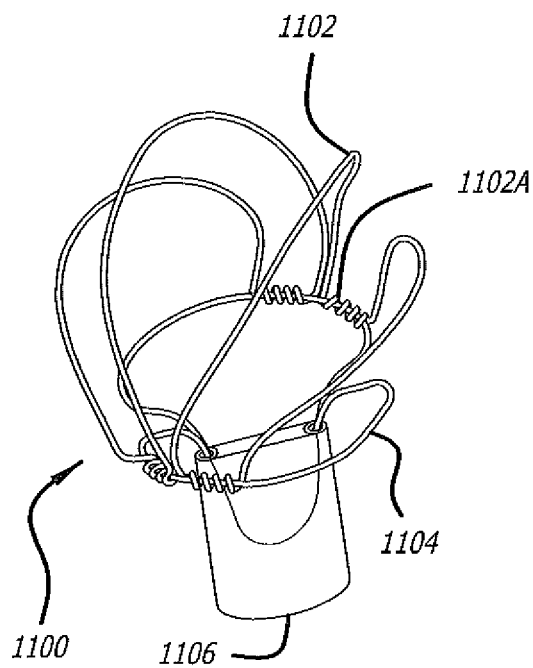
FIGS. 23C and 23D illustrate various perspective views of the prosthesis of FIG. 20A.
Figure 23D:
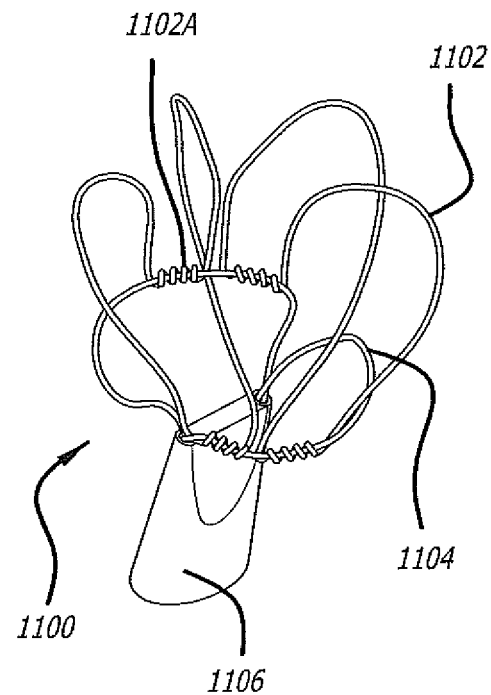

FIGS. 22A-22C illustrate yet another preferred embodiment of a prosthesis 1000 according to the present invention. Generally, this prosthesis 1000 is similar to the embodiments previously described in this specification, such as prosthesis 600 of FIGS. 17A-17D, including anchoring wires 1002, pocket support wires 1004, and pocket 10006 having a radial shape.

In addition to these similarities, the prosthesis 1000 includes region 1002A of anchoring wires 1002 that curve towards the open end of the pocket 1006. When expanded within the left atrium 126, the region 1002A of the present invention at least partially contacts the annulus of the mitral valve 120. This annulus support prevents the pocket 1006 from being pushed past the mitral valve 120 into the left ventricle 128, maintaining the overall vertical position of the prosthesis within the left atrium 120. In this respect, the anchoring wires 1002 can more generally be described as an anchoring framework or an anchoring structure.

FIGS. 23A-23D

Turning now to FIGS. 23A-23D, yet another preferred embodiment of a prosthesis 1100 according to the present invention is shown. Again, this prosthesis is generally similar to the previous embodiments described in this specification, including a pocket 1106 having an elongated shape, anchoring wires 1102, and lower loops 1104 that partially support the pocket 1106 and extent out from a top portion of the pocket 1106.

However, the free ends of the anchoring wires 1102 are wound around lower loops 1104, allowing the loops of anchoring wire 1102 to pivot on the lower loops 1104 to achieve more complex anchoring configurations. By achieve more complex anchoring configurations, the prosthesis 1100 can provide better support and therefore more constant positioning of the pocket 1106 over time. In this regard, the anchoring wires 1102 can more generally be described as an anchoring framework or an anchoring structure.

FIGS. 24A-24E

FIGS. 24A-24E illustrate another preferred embodiment of a prosthesis 1200 according to the present invention, having a pocket 1206 with an elongated shape, a pivot loop 1204 that is part of an unseen pocket support wire within the pocket 1206, and an anchoring wire 1202 having a region 1210 wound around the pivot loop 1204 to form a freely rotating pivot 1212.

Figure 24A:
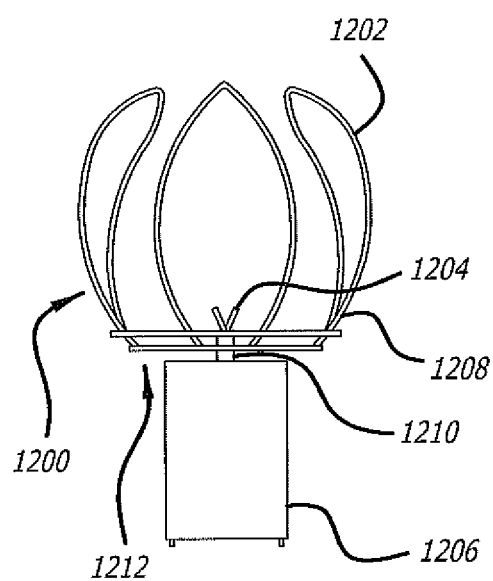
FIG. 24A illustrates a front view of a prosthesis according to another preferred embodiment of the present invention.
Figure 24B:
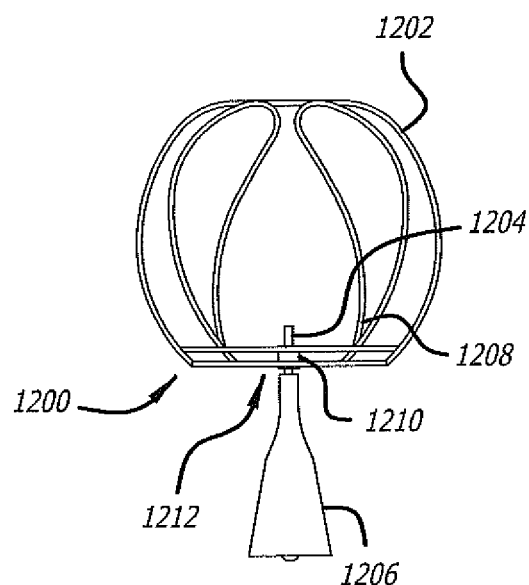
FIG. 24B illustrates a side view of the prosthesis of FIG. 23A.
Figure 24C:
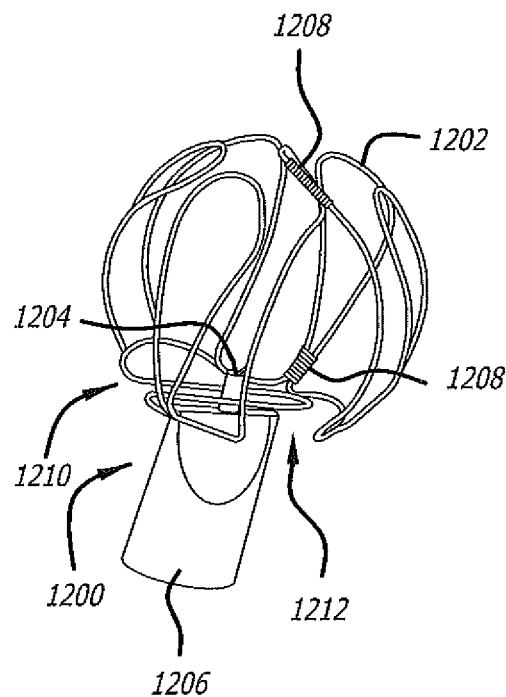
FIGS. 24C and 24D illustrate various perspective views of the prosthesis of FIG. 20A.
Figure 24D:
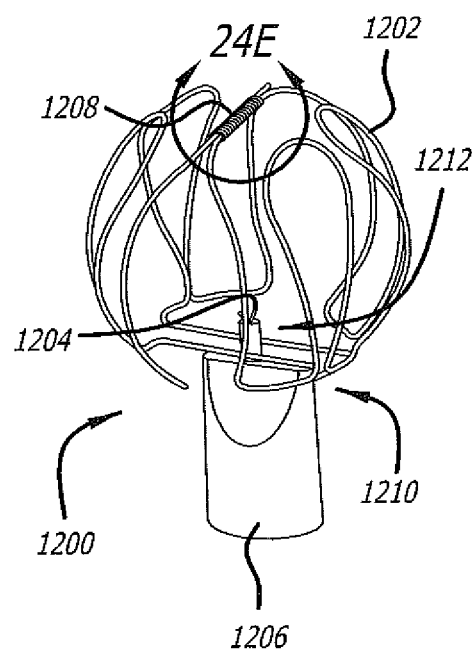
Figure 24E:
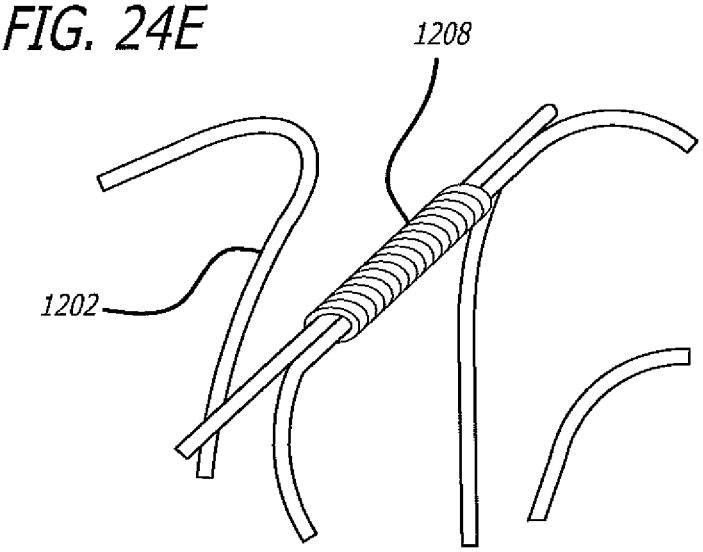
FIG. 24E illustrates an enlarged view of area 24E in FIG. 24D.

To achieve additional complexity with the design of the anchoring wire 1202, portions of the anchoring wire fixed to each other with knitting 1208, as best seen in FIG. 24E. By achieving additional complexity and looping structures, the prosthesis 1200 may be better able to anchor and therefore secure itself within the left atrium 126. Further, the knitting 1208 allows the bound regions of the anchoring wire 1202 to hinge relative to each other, which can allow more efficient packing within a delivery catheter 110 or more complex deployment strategies within the left ventricle 126. In this respect, the anchoring wire 1202 can more generally be described as an anchoring framework or an anchoring structure.

FIG. 25

Figure 25:
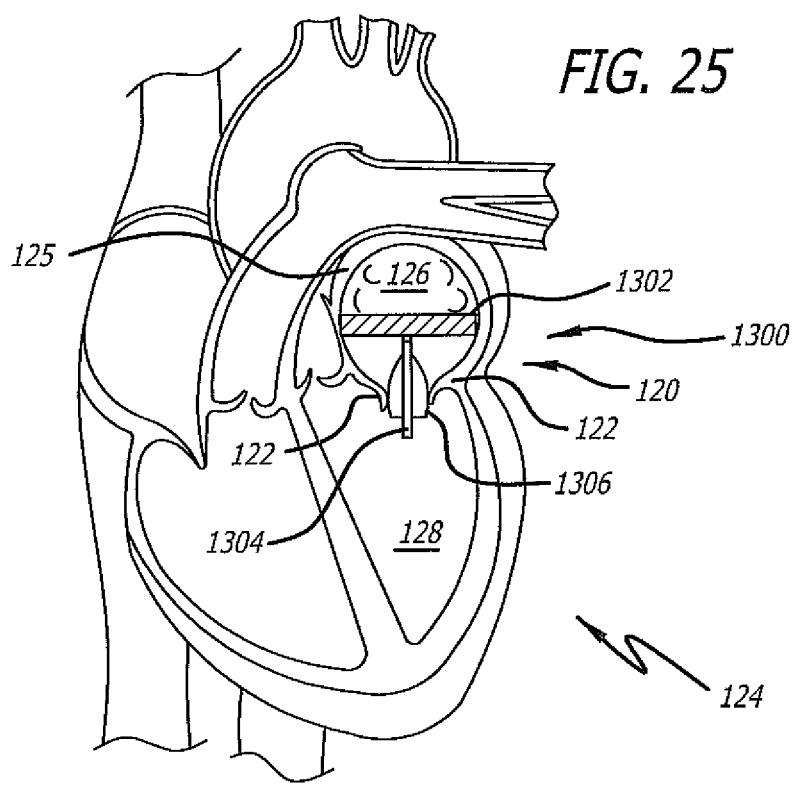
FIG. 25 illustrates a side view of a prosthesis within a heart according to another preferred embodiment of the present invention.

Turning to FIG. 25, yet another preferred embodiment of a prosthesis 1300 is illustrated according to the present invention. Specifically, prosthesis 1300 demonstrates a pocket 1306 having pocket supports 1304, generally similar to the embodiments previously described in this specification, and further including a stent anchor 1302 coupled to the pocket supports 1304. In this respect, the stent anchor 1302 can more generally be described as an anchoring framework or an anchoring structure.

The stent anchor 1302 can be composed of a variety of different materials and structures as is known in the art. For example, some stent techniques can be seen in U.S. Pat. Nos. 6,936,067; 6,929,658; 6,926,743; 6,923,828; and 6,902,575; the contents of each are herein incorporated by reference.

FIGS. 26A-26B

Figure 26B:
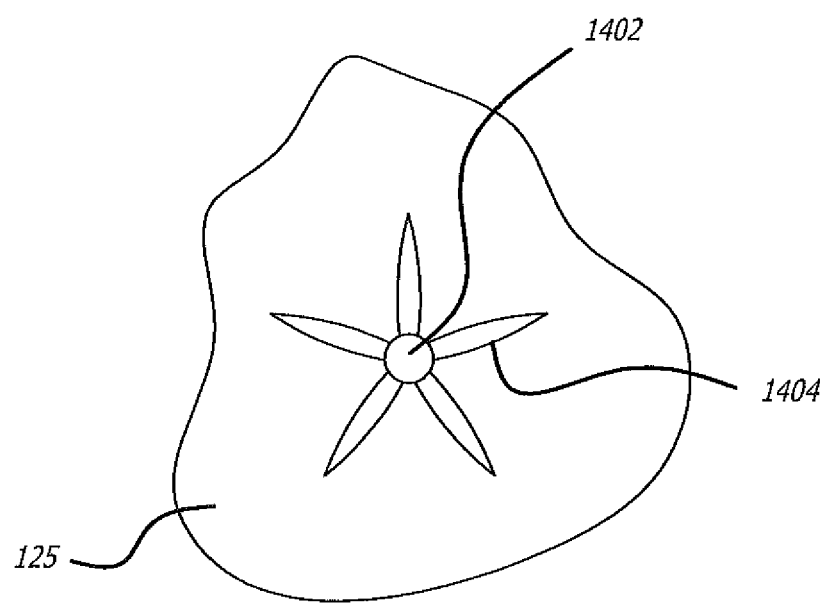
FIG. 26B illustrates a cross-sectional view of the prosthesis of FIG. 26A.
Figure 26A:
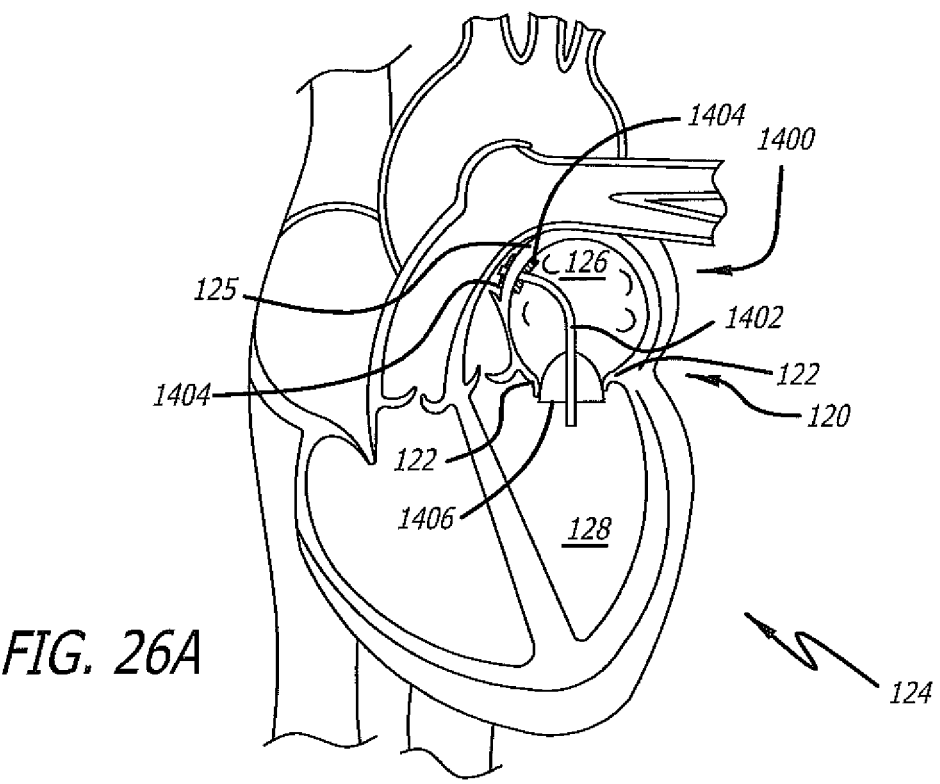
FIG. 26A illustrates a side view of a prosthesis within a heart according to another preferred embodiment of the present invention.

Turning to FIGS. 26A and 26B, yet another preferred embodiment of a prosthesis 1400 is illustrated according to the present invention, which includes an alternative anchoring and positioning system for a pocket 1406. Specifically, a positioning arm 1402 anchors within the atrial septum 125, having multiple septum attachment arms 1402 that extend from the base of the positioning arm 1402 and press against both the right and left sides of the atrial septum 125. Preferably, the septum attachment arms 1402 are similar in size and shape to those in atrial septal closure devices known in the art. To this end, the positioning arm 1402 can more generally be described as an anchoring framework or an anchoring structure.

In this respect, the prosthesis 1400 can be delivered via an incision in the atrial septum 125, first positioning the pocket 1406 within the mitral valve 120, then extending the septum attachment arms 1404 against both the left and right sides of the atrial septum 125 for anchoring support. The positioning arm 1402 substantially occludes the incision within the atrial septum 125, while the septum attachment arms 1402 retain the septal tissue around the positioning arm 1402, preventing blood from passing between through the septum 125.

While the preferred embodiments disclosed in this specification include expandable pockets, it should be understood that other designs can be used with the anchoring designs contemplated by the present invention. For example, a solid and preferably flexible plate member can alternatively be used, having a similar shape and size as described in regards to the pockets of the embodiments of this specification.

Preferably, the solid member is relatively soft, having a flexibility that allows some compression, especially when contacted by mitral valve leaflets. More preferably, the solid member could be created by adhering two pieces of pericardial tissue together and providing supporting members or wires similar to those described in regards to the pocket in the previous embodiments. In place of supporting members, Nitinol string may be attached to both the solid member and the left ventricle 128, preventing the solid member from moving into the left atrium 126. Alternatively, the solid member can be composed of a resilient, biocompatible polymer material such as polyurethane.

Preferably, the embodiments of this specification may also include flexible polymeric sheets, such as polyurethane, that connect the anchoring loops or anchoring wire that contact the left atrium 126. In this respect, the flexible sheets further decreases stress on the left atrium walls by more evenly distributing anchoring force.

It should be understood different elements of the embodiments of this application can be combine to form additional design contemplated by the present invention. For example, the septal anchoring prosthesis 1400 shown in FIGS. 26A and 26B may be combine with the anchoring structures shown with the prosthesis 900 of FIGS. 20A-20C.

While the embodiments disclosed in the present invention have been specifically described as used with the mitral valve of the heart, it is also contemplated that these embodiments may be adapted for use with other heart valves. For example, the anchoring structures can be modified to press against a different geometry within the heart and the pocket can be adapted to a different shaped valve, such as a tricuspid valve.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A mitral valve prosthesis comprising:
an anchor member shaped to conform to a geometry of a left atrium, the anchor member comprising an anchoring cage formed by laser cutting, the anchoring cage having a spherical expanded shape sized to be positioned entirely within the left atrium; and
an occluding member secured at a bottom of the anchor member, the occluding member comprising at least two pieces of flexible material stitched together, each piece of material having a rounded arch-shaped top portion and a straight bottom portion,
wherein the mitral valve prosthesis is compressible for percutaneous delivery and expandable for deployment in the left atrium with the occluding member proximate a native mitral valve and wherein the anchor member is shaped to maintain a substantially fixed position within the left atrium while applying an anchoring force against a wall of the left atrium, and wherein the occluding member is operable for opening during diastole and closing during systole.

2. The mitral valve prosthesis of claim 1, wherein the anchoring cage is laser cut from a single metal tube.

3. The mitral valve prosthesis of claim 1, wherein the mitral valve prosthesis is shaped such that leaflets of the native mitral valve are capable of opening and closing after the mitral valve prosthesis has been deployed in the left atrium.

4. The mitral valve prosthesis of claim 1, wherein the anchor member includes a shape memory material or nitinol.

5. The mitral valve prosthesis of claim 1, wherein the anchor member is sized to uniformly distribute the anchoring force along the wall of the left atrium.

6. The mitral valve prosthesis of claim 1, wherein the occluding member includes pericardial tissue, bovine tissue, polyurethane, fabric, biological material, or artificial material.

7. The mitral valve prosthesis of claim 1, further comprising support arms coupled to the anchor member, the support arms supporting the occluding member.

8. A mitral valve prosthesis for reducing regurgitation in a native mitral valve, comprising:

an anchor member comprising an anchoring cage comprising a plurality of wires, the anchoring cage having a spherical expanded shape sized to be positioned entirely within a left atrium, the anchoring cage cut from a single nitinol tube; and
an occluding member secured at a bottom of the anchor member, the occluding member comprising at least two pieces of flexible material stitched together, each piece of material having a rounded arch-shaped top portion and a straight bottom portion, the flexible material including pericardial tissue,
wherein the mitral valve prosthesis is compressible for percutaneous delivery and expandable for deployment in the left atrium with the occluding member proximate a native mitral valve, with the anchor member applying an anchoring force against a wall of the left atrium, and the occluding member operable for opening during diastole and closing during systole,
wherein the mitral valve prosthesis is shaped to allow leaflets of the native mitral valve to open and close when the mitral valve prosthesis is implanted in the left atrium.

\* \* \* \* \*